US007193038B2

(12) United States Patent
Tsubouchi et al.

(10) Patent No.: US 7,193,038 B2
(45) Date of Patent: Mar. 20, 2007

(54) EXTRACTION AND UTILIZATION OF CELL GROWTH-PROMOTING PEPTIDES FROM SILK PROTEIN

(75) Inventors: Kozo Tsubouchi, Ibaraki (JP); Hiromi Yamada, Tsukuba (JP)

(73) Assignee: National Institute of Agrobiological Sciences, Tsukuba (JP)

( * ) Notice: Subject to any disclaimer, the term of this patent is extended or adjusted under 35 U.S.C. 154(b) by 54 days.

(21) Appl. No.: 10/789,494

(22) Filed: Feb. 27, 2004

(65) Prior Publication Data

US 2005/0143296 A1 Jun. 30, 2005

(30) Foreign Application Priority Data

Feb. 28, 2003 (JP) ............................ 2003-055048

(51) Int. Cl.

| | |
|---|---|
| ***A61K 38/08*** | (2006.01) |
| ***A61K 38/10*** | (2006.01) |
| ***A61K 38/16*** | (2006.01) |
| ***C07K 7/06*** | (2006.01) |
| ***C07K 7/08*** | (2006.01) |
| ***C07K 14/00*** | (2006.01) |

(52) U.S. Cl. ...................... 530/324; 435/402; 435/404; 514/12; 514/13; 514/14; 514/17; 530/300; 530/326; 530/327; 530/329; 530/353

(58) Field of Classification Search ..................... None
See application file for complete search history.

(56) References Cited

U.S. PATENT DOCUMENTS 5,278,063 A * 1/1994 Hubbell et al. ............. 435/402
5,763,399 A * 6/1998 Lee ............................ 514/12
6,037,158 A * 3/2000 Hummel et al. ............ 435/190
2005/0089552 A1* 4/2005 Altman et al. .............. 424/445

FOREIGN PATENT DOCUMENTS

JP 6-292595 A * 10/1994

OTHER PUBLICATIONS

Yamada et al. Identification of fibroin-derived peptides . . . Biomaterials. 2004, vol. 25, pp. 467-472 (published Aug. 2003).*

* cited by examiner

*Primary Examiner*—Jeffrey Edwin Russel
(74) *Attorney, Agent, or Firm*—Flynn, Thiel, Boutell & Tanis, P.C.

(57) ABSTRACT

Peptides are provided having an excellent safety, stability due to relatively low molecular weights thereof, and cell growth promotion, which are different from cell growth factors produced by abnormal cells such as tumor cells. Peptide compositions which are excellent in promoting cell growth containing partial peptides of one or more peptide chains selected from peptide chains forming noncrystalline portions constituting silk protein. The partial peptides have specific amino acid sequences formed of four to forty amino acid residues. This invention has succeeded in providing novel peptides excellent for cell growth by separating and fractionating peptides, having specific amino acid sequences of molecular weights not higher than 10,000, preferably ranging from 4,000 to 400, from the noncrystalline portions of silk protein as well as by synthesizing peptides similar to such peptides. These peptides may be used for biomaterials such as a cell adhesion agent, cell growth-promoting agent, wound healing promoting agent, skin care material like cosmetic material or the like, and cell culture substrate.

6 Claims, No Drawings

SEQUENCE LISTING

```
<160> NUMBER OF SEQ ID NOS: 85

<210> SEQ ID NO 1
<211> LENGTH: 10
<212> TYPE: PRT
<213> ORGANISM: Bombyx mori

<400> SEQUENCE: 1

Val Ile Thr Thr Asp Ser Asp Gly Asn Glu
                5                   10


<210> SEQ ID NO 2
<211> LENGTH: 8
<212> TYPE: PRT
<213> ORGANISM: Bombyx mori

<400> SEQUENCE: 2

Asn Ile Asn Asp Phe Asp Glu Asp
                5


<210> SEQ ID NO 3
<211> LENGTH: 23
<212> TYPE: PRT
<213> ORGANISM: Bombyx mori

<400> SEQUENCE: 3

Ala Ala Ser Ser Val Ser Ser Ala Ser Ser Arg Ser Tyr Asp Tyr Ser
                5                   10                  15

Arg Arg Asn Val Arg Lys Asn
             20


<210> SEQ ID NO 4
<211> LENGTH: 29
<212> TYPE: PRT
<213> ORGANISM: Bombyx mori

<400> SEQUENCE: 4
```

-continued

```
Gly Ser Ser Gly Phe Gly Pro Tyr Val Ala His Gly Gly Tyr Ser Gly
                5                   10                  15

Tyr Glu Tyr Ala Trp Ser Ser Glu Ser Asp Phe Gly Thr
            20                  25


<210> SEQ ID NO 5
<211> LENGTH: 12
<212> TYPE: PRT
<213> ORGANISM: Antheraea yamamai

<400> SEQUENCE: 5

Tyr Gly Trp Gly Asp Gly Gly Tyr Gly Ser Asp Ser
                5                   10


<210> SEQ ID NO 6
<211> LENGTH: 6
<212> TYPE: PRT
<213> ORGANISM: Antheraea yamamai

<400> SEQUENCE: 6

Asp Glu Tyr Val Asp Asn
                5


<210> SEQ ID NO 7
<211> LENGTH: 20
<212> TYPE: PRT
<213> ORGANISM: Antheraea yamamai

<400> SEQUENCE: 7

Val Glu Thr Ile Val Leu Glu Glu Asp Pro Tyr Gly His Glu Asp Ile
                5                   10                  15

Tyr Glu Glu Asp
            20


<210> SEQ ID NO 8
<211> LENGTH: 13
<212> TYPE: PRT
<213> ORGANISM: Antheraea yamamai

<400> SEQUENCE: 8

Asp Asp Gly Phe Val Leu Asp Gly Gly Tyr Asp Ser Glu
                5                   10


<210> SEQ ID NO 9
<211> LENGTH: 151
<212> TYPE: PRT
<213> ORGANISM: Bombyx mori

<400> SEQUENCE: 9

Met Arg Val Lys Thr Phe Val Ile Leu Cys Cys Ala Leu Gln Tyr Val
                5                   10                  15

Ala Tyr Thr Asn Ala Asn Ile Asn Asp Phe Asp Glu Asp Tyr Phe Gly
            20                  25                  30

Ser Asp Val Thr Val Gln Ser Ser Asn Thr Thr Asp Glu Ile Ile Arg
        35                  40                  45

Asp Ala Ser Gly Ala Val Ile Glu Glu Gln Ile Thr Thr Lys Lys Met
    50                  55                  60

Gln Arg Lys Asn Lys Asn His Gly Ile Leu Gly Lys Asn Glu Lys Met
65                  70                  75                  80

Ile Lys Thr Phe Val Ile Thr Thr Asp Ser Asp Gly Asn Glu Ser Ile
                85                  90                  95
```

-continued

```
Val Glu Glu Asp Val Leu Met Lys Thr Leu Ser Asp Gly Thr Val Ala
            100                 105                 110

Gln Ser Tyr Val Ala Ala Asp Ala Gly Ala Tyr Ser Gln Ser Gly Pro
        115                 120                 125

Tyr Val Ser Asn Ser Gly Tyr Ser Thr His Gln Gly Tyr Thr Ser Asp
    130                 135                 140

Phe Ser Thr Ser Ala Ala Val
145                 150
```

<210> SEQ ID NO 10
<211> LENGTH: 30
<212> TYPE: PRT
<213> ORGANISM: Bombyx mori

<400> SEQUENCE: 10

```
Gly Ser Ser Gly Phe Gly Pro Tyr Val Ala Asn Gly Gly Tyr Ser Arg
                5                   10                  15

Ser Asp Gly Tyr Glu Tyr Ala Trp Ser Ser Asp Phe Gly Thr
            20                  25                  30
```

<210> SEQ ID NO 11
<211> LENGTH: 29
<212> TYPE: PRT
<213> ORGANISM: Bombyx mori

<400> SEQUENCE: 11

```
Gly Ser Ser Gly Phe Gly Pro Tyr Val Ala His Gly Gly Tyr Ser Gly
                5                   10                  15

Tyr Glu Tyr Ala Trp Ser Ser Glu Ser Asp Phe Gly Thr
            20                  25
```

<210> SEQ ID NO 12
<211> LENGTH: 29
<212> TYPE: PRT
<213> ORGANISM: Bombyx mori

<400> SEQUENCE: 12

```
Gly Ser Ser Gly Phe Gly Pro Tyr Val Ala Asn Gly Gly Tyr Ser Gly
                5                   10                  15

Tyr Glu Tyr Ala Trp Ser Ser Glu Ser Asp Phe Gly Thr
            20                  25
```

<210> SEQ ID NO 13
<211> LENGTH: 29
<212> TYPE: PRT
<213> ORGANISM: Bombyx mori

<400> SEQUENCE: 13

```
Gly Ser Ser Gly Phe Gly Pro Tyr Val Ala His Gly Gly Tyr Ser Gly
                5                   10                  15

Tyr Glu Tyr Ala Trp Ser Ser Glu Ser Asp Phe Gly Thr
            20                  25
```

<210> SEQ ID NO 14
<211> LENGTH: 29
<212> TYPE: PRT
<213> ORGANISM: Bombyx mori

<400> SEQUENCE: 14

```
Gly Ser Ser Gly Phe Gly Pro Tyr Val Ala His Gly Gly Tyr Ser Gly
1               5                   10                  15
```

-continued

```
Tyr Glu Tyr Ala Trp Ser Ser Glu Ser Asp Phe Gly Thr
            20                  25


<210> SEQ ID NO 15
<211> LENGTH: 29
<212> TYPE: PRT
<213> ORGANISM: Bombyx mori

<400> SEQUENCE: 15

Gly Ser Ser Gly Phe Gly Pro Tyr Val Ala Asn Gly Gly Tyr Ser Gly
                5                   10                  15

Tyr Glu Tyr Ala Trp Ser Ser Glu Ser Asp Phe Gly Thr
            20                  25


<210> SEQ ID NO 16
<211> LENGTH: 29
<212> TYPE: PRT
<213> ORGANISM: Bombyx mori

<400> SEQUENCE: 16

Gly Ser Ser Gly Phe Gly Pro Tyr Val Ala Asn Gly Gly Tyr Ser Gly
                5                   10                  15

Tyr Glu Tyr Ala Trp Ser Ser Glu Ser Asp Phe Gly Thr
            20                  25


<210> SEQ ID NO 17
<211> LENGTH: 29
<212> TYPE: PRT
<213> ORGANISM: Bombyx mori

<400> SEQUENCE: 17

Gly Ser Ser Gly Phe Gly Pro Tyr Val Ala Asn Gly Gly Tyr Ser Gly
                5                   10                  15

Tyr Glu Tyr Ala Trp Ser Ser Glu Ser Asp Phe Gly Thr
            20                  25


<210> SEQ ID NO 18
<211> LENGTH: 28
<212> TYPE: PRT
<213> ORGANISM: Bombyx mori

<400> SEQUENCE: 18

Gly Ser Ser Gly Phe Gly Pro Tyr Val Asn Gly Gly Tyr Ser Gly Tyr
                5                   10                  15

Glu Tyr Ala Trp Ser Ser Glu Ser Asp Phe Gly Thr
            20                  25


<210> SEQ ID NO 19
<211> LENGTH: 29
<212> TYPE: PRT
<213> ORGANISM: Bombyx mori

<400> SEQUENCE: 19

Gly Ser Ser Gly Phe Gly Pro Tyr Val Ala Asn Gly Gly Tyr Ser Gly
                5                   10                  15

Tyr Glu Tyr Ala Trp Ser Ser Glu Ser Asp Phe Gly Thr
            20                  25


<210> SEQ ID NO 20
<211> LENGTH: 32
<212> TYPE: PRT
<213> ORGANISM: Bombyx mori
```

-continued

<400> SEQUENCE: 20

Gly Ser Ser Gly Phe Gly Pro Tyr Val Ala Asn Gly Gly Tyr Ser Arg
1 5 10 15

Arg Glu Gly Tyr Glu Tyr Ala Trp Ser Ser Lys Ser Asp Phe Glu Thr
20 25 30

<210> SEQ ID NO 21
<211> LENGTH: 43
<212> TYPE: PRT
<213> ORGANISM: Bombyx mori

<400> SEQUENCE: 21

Ala Ala Ser Ser Val Ser Ser Ala Ser Ser Arg Ser Tyr Asp Tyr Ser
5 10 15

Arg Arg Asn Val Arg Lys Asn Cys Gly Ile Pro Arg Arg Gln Leu Val
20 25 30

Val Lys Phe Arg Ala Leu Pro Cys Val Asn Cys
35 40

<210> SEQ ID NO 22
<211> LENGTH: 262
<212> TYPE: PRT
<213> ORGANISM: Bombyx mori

<400> SEQUENCE: 22

Met Lys Pro Ile Phe Leu Val Leu Leu Val Ala Thr Ser Ala Tyr Ala
5 10 15

Ala Pro Ser Val Thr Ile Asn Gln Tyr Ser Asp Asn Glu Ile Pro Arg
20 25 30

Asp Ile Asp Asp Gly Lys Ala Ser Ser Val Ile Ser Arg Ala Trp Asp
35 40 45

Tyr Val Asp Asp Thr Asp Lys Ser Ile Ala Ile Leu Asn Val Gln Glu
50 55 60

Ile Leu Lys Asp Met Ala Ser Gln Gly Asp Tyr Ala Ser Gln Ala Ser
65 70 75 80

Ser Val Ala Gln Thr Ala Gly Ile Ile Ala His Leu Ser Ala Gly Ile
85 90 95

Pro Gly Asp Ala Cys Ala Ala Ala Asn Val Ile Asn Ser Tyr Thr Asp
100 105 110

Gly Val Arg Ser Gly Asn Phe Ala Gly Phe Arg Gln Ser Leu Gly Pro
115 120 125

Phe Phe Gly His Val Gly Gln Asn Leu Asn Leu Ile Asn Gln Leu Val
130 135 140

Ile Asn Pro Gly Gln Leu Arg Tyr Ser Val Gly Pro Ala Leu Gly Cys
145 150 155 160

Ala Gly Gly Gly Arg Ile Tyr Asp Phe Glu Ala Ala Trp Asp Ala Ile
165 170 175

Leu Ala Ser Ser Asp Ser Ser Phe Leu Asn Glu Glu Tyr Cys Ile Val
180 185 190

Lys Arg Leu Tyr Asn Ser Arg Asn Ser Gln Ser Asn Asn Ile Ala Ala
195 200 205

Tyr Ile Thr Ala His Leu Leu Pro Pro Val Ala Gln Val Phe His Gln
210 215 220

Ser Ala Gly Ser Ile Thr Asp Leu Leu Arg Gly Val Gly Asn Gly Asn
225 230 235 240

-continued

Asp Ala Thr Gly Leu Val Ala Asn Ala Gln Arg Tyr Ile Ala Gln Ala
                245                 250                 255

Ala Ser Gln Val His Val
            260

<210> SEQ ID NO 23
<211> LENGTH: 120
<212> TYPE: PRT
<213> ORGANISM: Antheraea yamamai

<400> SEQUENCE: 23

Met Arg Val Thr Ala Phe Val Ile Leu Cys Cys Ala Leu Gln Tyr Ala
                5                   10                  15

Thr Ala Asn Asn Leu His His His Asp Glu Tyr Val Asp Asn His Gly
            20                  25                  30

Gln Leu Val Glu Arg Phe Thr Thr Arg Lys His Tyr Glu Arg Asn Ala
        35                  40                  45

Ala Thr Arg Pro His Leu Ser Gly Asn Glu Arg Leu Val Glu Thr Ile
    50                  55                  60

Val Leu Glu Glu Asp Pro Tyr Gly His Glu Asp Ile Tyr Glu Glu Asp
65                  70                  75                  80

Val Val Ile Asn Arg Val Pro Gly Ala Ser Ser Ser Ala Ala Ala Ala
                85                  90                  95

Ser Ser Ala Ser Ala Gly Ser Gly Gln Thr Ile Ile Val Glu Arg Gln
            100                 105                 110

Ala Ser His Gly Ala Gly Gly Ala
        115                 120

<210> SEQ ID NO 24
<211> LENGTH: 16
<212> TYPE: PRT
<213> ORGANISM: Antheraea yamamai

<400> SEQUENCE: 24

Ala Gly Ala Ala Ala Gly Ala Ala Ala Gly Ser Ser Ala Arg Gly Gly
                5                   10                  15

<210> SEQ ID NO 25
<211> LENGTH: 45
<212> TYPE: PRT
<213> ORGANISM: Antheraea yamamai

<400> SEQUENCE: 25

Ser Gly Phe Tyr Glu Thr His Asp Ser Tyr Ser Ser Tyr Gly Ser Gly
                5                   10                  15

Ser Ser Ser Ala Ala Ala Ala Ser Ser Gly Ala Gly Gly Ala Gly Gly
            20                  25                  30

Gly Tyr Gly Trp Gly Asp Gly Gly Tyr Gly Ser Asp Ser
        35                  40                  45

<210> SEQ ID NO 26
<211> LENGTH: 17
<212> TYPE: PRT
<213> ORGANISM: Anthraea yamamai

<400> SEQUENCE: 26

Gly Ser Gly Ala Gly Gly Arg Gly Asp Gly Gly Tyr Gly Ser Gly Ser
                5                   10                  15

Ser

-continued

<210> SEQ ID NO 27
<211> LENGTH: 27
<212> TYPE: PRT
<213> ORGANISM: Antheraea yamamai

<400> SEQUENCE: 27

```
Arg Arg Ala Gly His Asp His Ala Ala Gly Ser Ser Gly Gly Gly Tyr
                5                   10                  15

Ser Trp Asp Tyr Ser Ser Tyr Gly Ser Glu Ser
            20                  25
```

<210> SEQ ID NO 28
<211> LENGTH: 23
<212> TYPE: PRT
<213> ORGANISM: Antheraea yamamai

<400> SEQUENCE: 28

```
Gly Ser Gly Ala Gly Gly Val Gly Gly Gly Tyr Gly Gly Gly Asp Gly
                5                   10                  15

Gly Tyr Gly Ser Gly Ser Ser
            20
```

<210> SEQ ID NO 29
<211> LENGTH: 11
<212> TYPE: PRT
<213> ORGANISM: Antheraea yamamai

<400> SEQUENCE: 29

```
Arg Arg Ala Gly His Asp Arg Ala Ala Gly Ser
                5                   10
```

<210> SEQ ID NO 30
<211> LENGTH: 21
<212> TYPE: PRT
<213> ORGANISM: Antheraea yamamai

<400> SEQUENCE: 30

```
Ser Gly Ala Gly Gly Ser Gly Gly Gly Tyr Gly Trp Gly Asp Gly Gly
                5                   10                  15

Tyr Gly Ser Asp Ser
            20
```

<210> SEQ ID NO 31
<211> LENGTH: 8
<212> TYPE: PRT
<213> ORGANISM: Antheraea yamamai

<400> SEQUENCE: 31

```
Gly Ser Gly Ala Gly Arg Ala Gly
                5
```

<210> SEQ ID NO 32
<211> LENGTH: 14
<212> TYPE: PRT
<213> ORGANISM: Antheraea yamamai

<400> SEQUENCE: 32

```
Gly Asp Tyr Gly Trp Gly Asp Gly Gly Tyr Gly Ser Asp Ser
                5                   10
```

<210> SEQ ID NO 33
<211> LENGTH: 11
<212> TYPE: PRT

-continued

<213> ORGANISM: Antheraea yamamai

<400> SEQUENCE: 33

```
Arg Gln Ala Gly His Glu Arg Ala Ala Gly Ser
                5                   10
```

<210> SEQ ID NO 34
<211> LENGTH: 21
<212> TYPE: PRT
<213> ORGANISM: Antheraea yamamai

<400> SEQUENCE: 34

```
Ser Gly Ala Gly Gly Ser Gly Arg Gly Tyr Gly Trp Gly Asp Gly Gly
                5                   10                  15

Tyr Gly Ser Asp Ser
            20
```

<210> SEQ ID NO 35
<211> LENGTH: 21
<212> TYPE: PRT
<213> ORGANISM: Antheraea yamamai

<400> SEQUENCE: 35

```
Gly Ser Gly Ala Gly Gly Ala Gly Gly Asp Tyr Gly Trp Gly Asp Gly
                5                   10                  15

Gly Tyr Gly Ser Asp
            20
```

<210> SEQ ID NO 36
<211> LENGTH: 22
<212> TYPE: PRT
<213> ORGANISM: Antheraea yamamai

<400> SEQUENCE: 36

```
Gly Ser Gly Ala Gly Gly Ala Gly Gly Asp Tyr Gly Trp Gly Asp Gly
                5                   10                  15

Gly Tyr Gly Ser Asp Ser
            20
```

<210> SEQ ID NO 37
<211> LENGTH: 21
<212> TYPE: PRT
<213> ORGANISM: Antheraea yamamai

<400> SEQUENCE: 37

```
Ser Gly Ala Gly Gly Ala Gly Gly Gly Tyr Gly Trp Gly Asp Gly Gly
                5                   10                  15

Tyr Gly Ser Asp Ser
            20
```

<210> SEQ ID NO 38
<211> LENGTH: 16
<212> TYPE: PRT
<213> ORGANISM: Antheraea yamamai

<400> SEQUENCE: 38

```
Ser Gly Ala Gly Gly Ala Gly Gly Tyr Gly Gly Tyr Gly Ser Asp Ser
                5                   10                  15
```

<210> SEQ ID NO 39
<211> LENGTH: 21
<212> TYPE: PRT
<213> ORGANISM: Antheraea yamamai -continued

<400> SEQUENCE: 39

Ser Gly Ala Gly Gly Ser Gly Gly Gly Tyr Gly Trp Gly Asp Gly Gly
5 10 15

Tyr Gly Ser Gly Ser
20

<210> SEQ ID NO 40
<211> LENGTH: 22
<212> TYPE: PRT
<213> ORGANISM: Antheraea yamamai

<400> SEQUENCE: 40

Gly Ser Gly Ala Gly Gly Val Gly Gly Gly Tyr Gly Trp Gly Asp Gly
5 10 15

Gly Tyr Gly Ser Asp Ser
20

<210> SEQ ID NO 41
<211> LENGTH: 16
<212> TYPE: PRT
<213> ORGANISM: Antheraea yamamai

<400> SEQUENCE: 41

Ser Gly Ala Gly Gly Arg Gly Asp Gly Gly Tyr Gly Ser Gly Ser Ser
5 10 15

<210> SEQ ID NO 42
<211> LENGTH: 22
<212> TYPE: PRT
<213> ORGANISM: Antheraea yamamai

<400> SEQUENCE: 42

Gly Ser Gly Ala Gly Gly Ala Gly Gly Gly Tyr Gly Trp Gly Asp Gly
5 10 15

Gly Tyr Gly Ser Asp Ser
20

<210> SEQ ID NO 43
<211> LENGTH: 11
<212> TYPE: PRT
<213> ORGANISM: Antheraea yamamai

<400> SEQUENCE: 43

Arg Arg Ala Gly His Asp Arg Ala Ala Gly Cys
5 10

<210> SEQ ID NO 44
<211> LENGTH: 21
<212> TYPE: PRT
<213> ORGANISM: Antheraea yamamai

<400> SEQUENCE: 44

Ser Gly Ala Gly Gly Thr Gly Gly Gly Tyr Gly Trp Gly Asp Gly Gly
5 10 15

Tyr Gly Ser Asp Ser
20

<210> SEQ ID NO 45
<211> LENGTH: 21
<212> TYPE: PRT
<213> ORGANISM: Antheraea yamamai -continued

<400> SEQUENCE: 45

Ser Gly Ala Gly Gly Ser Gly Gly Gly Tyr Gly Trp Gly Asp Gly Gly
5 10 15

Tyr Gly Ser Asn Ser
20

<210> SEQ ID NO 46
<211> LENGTH: 21
<212> TYPE: PRT
<213> ORGANISM: Antheraea yamamai

<400> SEQUENCE: 46

Ser Gly Ala Gly Arg Ser Gly Gly Gly Tyr Gly Trp Gly Asp Gly Gly
5 10 15

Tyr Ser Ser Asp Ser
20

<210> SEQ ID NO 47
<211> LENGTH: 16
<212> TYPE: PRT
<213> ORGANISM: Antheraea yamamai

<400> SEQUENCE: 47

Ser Gly Ala Gly Gly Ser Gly Gly Tyr Gly Gly Tyr Gly Ser Asp Ser
5 10 15

<210> SEQ ID NO 48
<211> LENGTH: 25
<212> TYPE: PRT
<213> ORGANISM: Antheraea yamamai

<400> SEQUENCE: 48

Gly Ser Gly Ala Gly Gly Val Gly Gly Gly Tyr Gly Trp Gly Asp Gly
5 10 15

Gly Tyr Gly Gly Tyr Gly Ser Asp Ser
20 25

<210> SEQ ID NO 49
<211> LENGTH: 23
<212> TYPE: PRT
<213> ORGANISM: Antheraea yamamai

<400> SEQUENCE: 49

Gly Ser Gly Ala Gly Gly Val Gly Gly Gly Tyr Gly Arg Gly Asp Ser
5 10 15

Gly Tyr Gly Ser Gly Ser Ser
20

<210> SEQ ID NO 50
<211> LENGTH: 8
<212> TYPE: PRT
<213> ORGANISM: Antheraea yamamai

<400> SEQUENCE: 50

Gly His Gly Arg Ser Ser Gly Ser
5

<210> SEQ ID NO 51
<211> LENGTH: 21
<212> TYPE: PRT
<213> ORGANISM: Antheraea yamamai

<400> SEQUENCE: 51

-continued

```
Ser Gly Ala Gly Gly Ser Gly Gly Gly Tyr Gly Trp Asp Tyr Gly Ser
                5                   10                  15

Tyr Gly Ser Asp Ser
            20


<210> SEQ ID NO 52
<211> LENGTH: 22
<212> TYPE: PRT
<213> ORGANISM: Antheraea yamamai

<400> SEQUENCE: 52

Ser Ser Gly Ala Gly Gly Ser Gly Gly Gly Tyr Gly Trp Asp Tyr Gly
                5                   10                  15

Gly Tyr Gly Ser Asp Ser
            20


<210> SEQ ID NO 53
<211> LENGTH: 22
<212> TYPE: PRT
<213> ORGANISM: Antheraea yamamai

<400> SEQUENCE: 53

Gly Ser Gly Ala Gly Gly Ser Gly Gly Gly Tyr Gly Trp Gly Asp Gly
                5                   10                  15

Gly Tyr Gly Ser Asp Ser
            20


<210> SEQ ID NO 54
<211> LENGTH: 14
<212> TYPE: PRT
<213> ORGANISM: Antheraea yamamai

<400> SEQUENCE: 54

Ser Arg Arg Ala Gly His Asp Arg Ala Tyr Gly Ala Gly Ser
                5                   10


<210> SEQ ID NO 55
<211> LENGTH: 28
<212> TYPE: PRT
<213> ORGANISM: Antheraea yamamai

<400> SEQUENCE: 55

Gly Ala Gly Ala Ser Arg Pro Val Gly Ile Tyr Gly Thr Asp Asp Gly
                5                   10                  15

Phe Val Leu Asp Gly Gly Tyr Asp Ser Glu Gly Ser
            20                  25


<210> SEQ ID NO 56
<211> LENGTH: 34
<212> TYPE: PRT
<213> ORGANISM: Antheraea yamamai

<400> SEQUENCE: 56

Ser Ser Ser Gly Arg Ser Thr Glu Gly His Pro Leu Leu Ser Ile Cys
                5                   10                  15

Cys Arg Pro Cys Ser His Arg His Ser Tyr Glu Ala Ser Arg Ile Ser
            20                  25                  30

Val His


<210> SEQ ID NO 57
<211> LENGTH: 22
```

<212> TYPE: PRT
<213> ORGANISM: Bombyx mori

<400> SEQUENCE: 57

Gly Ala Gly Ala Gly Ser Gly Ala Gly Ala Gly Ser Gly Ala Gly Ala
                5                   10                  15
Gly Tyr Gly Ala Gly Tyr
            20

<210> SEQ ID NO 58
<211> LENGTH: 22
<212> TYPE: PRT
<213> ORGANISM: Bombyx mori

<400> SEQUENCE: 58

Gly Ala Gly Ala Gly Ser Gly Ala Ala Ser Gly Ala Gly Ala Gly Ala
                5                   10                  15
Gly Ala Gly Ala Gly Thr
            20

<210> SEQ ID NO 59
<211> LENGTH: 23
<212> TYPE: PRT
<213> ORGANISM: Bombyx mori

<400> SEQUENCE: 59

Ala Ala Ser Ser Val Ser Ser Ala Ser Ser Arg Ser Tyr Asp Tyr Ser
                5                   10                  15
Arg Arg Asn Val Arg Lys Asn
            20

<210> SEQ ID NO 60
<211> LENGTH: 29
<212> TYPE: PRT
<213> ORGANISM: Bombyx mori

<400> SEQUENCE: 60

Gly Ser Ser Gly Phe Gly Pro Tyr Val Ala His Gly Gly Tyr Ser Gly
                5                   10                  15
Tyr Glu Tyr Ala Trp Ser Ser Glu Ser Asp Phe Gly Thr
            20                  25

<210> SEQ ID NO 61
<211> LENGTH: 10
<212> TYPE: PRT
<213> ORGANISM: Antheraea yamamai

<400> SEQUENCE: 61

Ala Ala Ala Ala Ala Ala Ala Ala Ala Ala
                5                   10

<210> SEQ ID NO 62
<211> LENGTH: 12
<212> TYPE: PRT
<213> ORGANISM: Antheraea yamamai

<400> SEQUENCE: 62

Tyr Gly Trp Gly Asp Gly Gly Tyr Gly Ser Asp Ser
                5                   10

<210> SEQ ID NO 63
<211> LENGTH: 16
<212> TYPE: PRT

-continued

<213> ORGANISM: Antheraea yamamai

<400> SEQUENCE: 63

Ser Gly Ala Gly Gly Ser Gly Gly Tyr Gly Gly Tyr Gly Ser Asp Ser
5 10 15

<210> SEQ ID NO 64
<211> LENGTH: 17
<212> TYPE: PRT
<213> ORGANISM: Antheraea yamamai

<400> SEQUENCE: 64

Gly Ser Gly Ala Gly Gly Arg Gly Asp Gly Gly Tyr Gly Ser Gly Ser
5 10 15

Ser

<210> SEQ ID NO 65
<211> LENGTH: 11
<212> TYPE: PRT
<213> ORGANISM: Antheraea yamamai

<400> SEQUENCE: 65

Arg Arg Ala Gly His Asp Arg Ala Ala Gly Ser
5 10

<210> SEQ ID NO 66
<211> LENGTH: 6
<212> TYPE: PRT
<213> ORGANISM: Antheraea yamamai

<400> SEQUENCE: 66

Asp Glu Tyr Val Asp Asn
5

<210> SEQ ID NO 67
<211> LENGTH: 20
<212> TYPE: PRT
<213> ORGANISM: Antheraea yamamai

<400> SEQUENCE: 67

Val Glu Thr Ile Val Leu Glu Glu Asp Pro Tyr Gly His Glu Asp Ile
5 10 15

Tyr Glu Glu Asp
20

<210> SEQ ID NO 68
<211> LENGTH: 13
<212> TYPE: PRT
<213> ORGANISM: Antheraea yamamai

<400> SEQUENCE: 68

Asp Asp Gly Phe Val Leu Asp Gly Gly Tyr Asp Ser Glu
5 10

<210> SEQ ID NO 69
<211> LENGTH: 6
<212> TYPE: PRT
<213> ORGANISM: Bombyx mori

<400> SEQUENCE: 69

Gly Ala Gly Ala Gly Ser
5

-continued

```
<210> SEQ ID NO 70
<211> LENGTH: 6
<212> TYPE: PRT
<213> ORGANISM: Bombyx mori

<400> SEQUENCE: 70

Asp Ser Asp Gly Asp Glu
                5


<210> SEQ ID NO 71
<211> LENGTH: 6
<212> TYPE: PRT
<213> ORGANISM: Bombyx mori

<400> SEQUENCE: 71

Asp Glu Asp Glu Asp Glu
                5


<210> SEQ ID NO 72
<211> LENGTH: 6
<212> TYPE: PRT
<213> ORGANISM: Bombyx mori

<400> SEQUENCE: 72

Glu Asp Glu Asp Glu Asp
                5


<210> SEQ ID NO 73
<211> LENGTH: 6
<212> TYPE: PRT
<213> ORGANISM: Bombyx mori

<400> SEQUENCE: 73

Ser Ser Glu Ser Ser Glu
                5


<210> SEQ ID NO 74
<211> LENGTH: 6
<212> TYPE: PRT
<213> ORGANISM: Bombyx mori

<400> SEQUENCE: 74

Tyr Gly Gly Tyr Glu Tyr
                5


<210> SEQ ID NO 75
<211> LENGTH: 7
<212> TYPE: PRT
<213> ORGANISM: Antheraea yamamai

<400> SEQUENCE: 75

Asp Gly Gly Tyr Gly Gly Asp
                5


<210> SEQ ID NO 76
<211> LENGTH: 6
<212> TYPE: PRT
<213> ORGANISM: Antheraea yamamai

<400> SEQUENCE: 76

Asp Glu Tyr Asp Glu Tyr
                5


<210> SEQ ID NO 77
<211> LENGTH: 8
```

-continued

<212> TYPE: PRT
<213> ORGANISM: Antheraea yamamai

<400> SEQUENCE: 77

Tyr Glu Glu Asp Tyr Glu Glu Asp
5

<210> SEQ ID NO 78
<211> LENGTH: 4
<212> TYPE: PRT
<213> ORGANISM: Artificial sequence
<220> FEATURE:
<223> OTHER INFORMATION: Cell growth promoting activity

<400> SEQUENCE: 78

Glu Glu Glu Glu

<210> SEQ ID NO 79
<211> LENGTH: 6
<212> TYPE: PRT
<213> ORGANISM: Artificial sequence
<220> FEATURE:
<223> OTHER INFORMATION: Cell growth promoting activity

<400> SEQUENCE: 79

Glu Glu Glu Glu Glu Glu
5

<210> SEQ ID NO 80
<211> LENGTH: 6
<212> TYPE: PRT
<213> ORGANISM: Artificial sequence
<220> FEATURE:
<223> OTHER INFORMATION: Cell growth promoting activity

<400> SEQUENCE: 80

Glu Tyr Glu Tyr Glu Tyr
5

<210> SEQ ID NO 81
<211> LENGTH: 6
<212> TYPE: PRT
<213> ORGANISM: Artificial sequence
<220> FEATURE:
<223> OTHER INFORMATION: Cell growth promoting activity

<400> SEQUENCE: 81

Glu Glu Tyr Glu Glu Tyr
5

<210> SEQ ID NO 82
<211> LENGTH: 6
<212> TYPE: PRT
<213> ORGANISM: Artificial sequence
<220> FEATURE:
<223> OTHER INFORMATION: Cell growth promoting activity

<400> SEQUENCE: 82

Tyr Tyr Tyr Tyr Tyr Tyr
5

<210> SEQ ID NO 83
<211> LENGTH: 6
<212> TYPE: PRT
<213> ORGANISM: Artificial sequence
<220> FEATURE:
<223> OTHER INFORMATION: Cell growth promoting activity -continued

```
<400> SEQUENCE: 83

Glu Gly Ser Glu Gly Ser
                5


<210> SEQ ID NO 84
<211> LENGTH: 10
<212> TYPE: PRT
<213> ORGANISM: Artificial sequence
<220> FEATURE:
<223> OTHER INFORMATION: Cell growth promoting activity

<400> SEQUENCE: 84

Glu Glu Glu Glu Glu Glu Glu Glu Glu Glu
                5                   10


<210> SEQ ID NO 85
<211> LENGTH: 4
<212> TYPE: PRT
<213> ORGANISM: Artificial sequence
<220> FEATURE:
<223> OTHER INFORMATION: Cell growth promoting activity

<400> SEQUENCE: 85

Tyr Tyr Tyr Tyr
```

EXTRACTION AND UTILIZATION OF CELL GROWTH-PROMOTING PEPTIDES FROM SILK PROTEIN

TECHNICAL FIELD

The present invention relates to peptides from silk protein which are excellent in promoting cell growth, a production method thereof, and application thereof to the fields of medicaments, quasi drugs, cosmetics, etc., as a material for skin care as well as to cell culture substrates as a biomaterial.

RELATED ART

Since silk threads have been used as a surgical suture from the old days, silk protein is regarded as a biocompatible material, and new developments focusing attention on this property have recently become active for its new uses in various fields.

For example, silk threads are solubilized to form an aqueous silk protein solution, followed by conversion to powder by precipitation, drying, grinding, etc., for additives to cosmetics; the aqueous silk protein solution is made into a film-like material by casting on a plate and the like for a cell culture bed or wound-covering and coating material; and the silk protein solution is made into a gel-like material for use in food and cosmetics. The developments of these uses are pursued.

Such developing examples include, for example, Kokai (Jpn. unexamined patent publication) 62-000415, Kokoku (examined patent publication) 01-044320, Kokai (Jpn. unexamined patent publication) 01-254164, Kokoku (examined patent publication) 06-004679, Kokai (Jpn. unexamined patent publication) 11-139986, Kokai (Jpn. unexamined patent publication) 11-276876, U.S. Pat. No. 2,997,758, U.S. Pat. No. 2,990,239, Kokai (Jpn. unexamined patent publication) 11-253155, Patent application 2002-230656, Patent application 2002-148849, Kokai (Jpn. unexamined patent publication) 2001-163899. (See patent literatures from 1 to 12)

During the development of new silk materials, it has become apparent that silk protein possesses various functions such as cell growth promotion, antioxidation, germicidal action, alcohol digestion and anticoagulation of blood.

However, it has not yet been elucidated which site or structure in silk protein is responsible for those functions.

The present inventors paid attention to the cell growth function associated with silk protein and have pursued the development and study of its function with the aim of utilizing cocoon filaments or silk threads as a skin care material for wound-covering materials, cosmetics and improved materials of synthetic fiber after these threads are solubilized and then converted into powder, film, gel and the like (for example, see patent literatures 8, 9, 10, 11 and 12).

In the course of the above development and study, it was found that the H and L-chains of fibroin and sericin, components constituting silk protein, have a growth-promoting action on fibroblasts originating from normal human skin (for example, see patent literatures 13, 14, and 15).

On the other hand, cocoon filaments are used as a fiber, besides the field of clothing, in the fields of, for example, medical care (surgical suture for surgery), cosmetics (puff) and the like by processing cocoons via various process steps into raw silk and further into silk fabrics, and it has recently been recognized that the molecular weight of silk protein decreases during the processing of cocoon and raw silk.

Moreover, also in the process step of converting cocoon filaments or silk threads into powder, film, gel or the like (particularly, the solubilizing step of cocoon filaments or silk threads), the molecular weight of silk protein was found to decrease (H. Yamada et al., Material Science & Engineering C, 14, p. 41–46 (2001)), (Tubouchi Kouzou, Yamada Hiromi, Takasu Yoko: the Japanese Society of Sericulture Science academic journal, Vol. 71, no. 1, P. 1–5 (2002)), (See nonpatent literature, nonpatent literature 2).

Silk proteins with their molecular weight decreased by such processes show a broad band with a smear in a molecular weight range between 10,000 and 200,000 daltons on an electrophoretogram.

Those with a molecular weight of less than 10,000 daltons are mostly removed during the steps of dialysis and the like, and in fact, their molecular weights are decreased up to amino acid and oligopeptide levels.

The silk proteins with lowered molecular weights were found to have a reduced growth-promoting activity for human cells or to inhibit the cell growth (see patent literature 11).

In other words, undegraded fibroin and undegraded sericin are excellent for promoting cell growth, whereas complex and heterogeneous cleavage of peptide bonds by treatment with an acid, alkali, light, heat, etc., during the processing of the cocoon resulted in inhibiting cell growth along with a reduction in their molecular weights.

Accordingly, for the purpose of utilizing the cell growth-promoting function of silk proteins, it is preferred to use undegraded fibroin or undegraded sericin, fibroin H-chain (molecular weight, ca. 350,000) or L-chain, sericin a (molecular weight, ca. 400,000) and the like in their undegraded states.

However, these three components (particularly, the H-chain and sericin a) have large molecular weights, and their stability in keeping their properties constant during prolonged storage is low.

Further, the L-chain is contained in fibroin only at less than 10% by weight and is small in quantity.

Furthermore, there is yet no report clarifying which portion of each of these three components possesses cell growth-promoting activity.

Patent Literature 1
Kokai (Jpn. unexamined patent publication) 62-000415

Patent Literature 2
Kokoku (examined patent publication) 01-044320

Patent Literature 3
Kokai (Jpn. unexamined patent publication) 01-254164

Patent Literature 4
Kokai (Jpn. unexamined patent publication) 04-202435

Patent Literature 5
Kokoku (examined patent publication) 06-004679

Patent Literature 6
Kokai (Jpn. unexamined patent publication) 11-139986

Patent Literature 7
Kokai (Jpn. unexamined patent publication) 11-276876

Patent Literature 8
U.S. Pat. No. 2,997,758

Patent Literature 9
U.S. Pat. No. 2,990,239

Patent Literature 10
Kokai (Jpn. unexamined patent publication) 11-253155

Patent Literature 11
Patent application 2002-230656

Patent Literature 12
Patent application 2002-148849

Patent Literature 13
Kokai (Jpn. unexamined patent publication) 2001-163899

Patent Literature 14
Patent application 2001-180169

Patent Literature 15
Kokai (Jpn. unexamined patent publication) 2002-128691

Nonpatent Literature 1
H. Yamada et al., Materials Science & Engineering C, 14, P. 41–46 (2001)

Nonpatent Literature 2
Tsubouchi Kouzou, Yamada Hiromi, Takasu Yoko: The Japanese Society of Sericulture Science academic journal Vol. 71, No. 1, P. 1–5 (2002)

Nonpatent Literature 3
Tashiro Yutaka and Otsuki Eiichi, Journal of Cell Biology, Vol. 46, P1 (1970)

The fibroin H-chain and the a component of sericin are excellent for promoting cell growth, while they have high molecular weights larger than 300,000 and tend to crystallize.

In comparison to these, the molecular weight of the fibroin L-chain is 25,000 and smaller than that of the H-chain or the a component, but it has a tendency to crystallize more easily than ordinary proteins.

In addition, the ratio of fibroin H-chain to L-chain by weight is about 13 (H-chain) to 1 (L-chain), and the percentage of the L-chain is very small.

Proteins having a high molecular weight and high crystallinity are unstable in aqueous solutions.

Furthermore, when medicaments or cosmetic additives containing an oily ingredient or the like are added to these proteins, gel formation may readily occur, turning to unstable physical properties, and their stability during prolonged storage (more than 1 year) is low.

On the other hand, substances which have a molecular weight lower than silk fibroin H-chain or sericin a and are excellent for cell growth include growth factors for various cells, for example, fibroblast growth factor (FGF) having a molecular weight ranging from 17,700 to 19,000.

These factors are secreted from tumors and cancerous cells, or from rapidly growing cells, and some of them are used as a therapeutic agent for skin ulcer (Fiblast Spray, Kaken Pharmaceutical Co., Ltd.), but their safety is a concern.

SUMMARY OF THE INVENTION

The present invention was accomplished to solve these problems.

Namely, an object of this invention is to obtain peptides having excellent safety, stability due to their relatively low molecular weights, and cell growth promotion, all of which are different from cell growth factors produced by abnormal cells such as tumor cells.

In order to solve the above problems, the present inventors have diligently conducted research and succeeded now in identifying that peptide chains located at specific sites of silk fibroin have a cell growth-promoting function, thus completing the present invention.

That is, the present invention is significant in the aspect (1) that peptide compositions excellent for promoting cell growth comprise partial peptides of one or more peptide chains selected from peptide chains forming noncrystalline portions constituting silk protein, where the partial peptides have specific amino acid sequences formed of four to forty amino acid residues.

More specifically, the present invention provides peptide compositions excellent for promoting cell growth comprising the partial peptides from one or more peptide chains selected from the respective peptide chains of the N-terminal portion (I), the noncrystalline portion (A) and the C-terminal portion (a) constituting the H-chain of silk fibroin from a domesticated silkworm, the peptide chain of the L-chain thereof, and the respective peptide chains of the N-terminal portion (I), noncrystalline portion (A) and C-terminal portion (a) constituting the silk fibroin from a wild silkworm belonging to the genus *Antheraea* such as *Antheraea yamamai*, where the partial peptides have specific amino acid sequences formed of 4 to 40 amino acid residues.

Further, a second aspect (2) provides a peptide composition where the peptide chains with the above specific amino acid sequences have any of the following amino acid sequences from (1) to (8):

```
(1) A-6-2  Val Ile Thr Thr Asp Ser Asp Gly Asn Glu                                (SEQ ID NO. 1)
                           5                   10

(2) A-6-6  Asn Ile Asn Asp Phe Asp Glu Asp                                        (SEQ ID NO. 2)
                           5

(3) SfHe   Ala Ala Ser Ser Val Ser Ser Ala Ser Ser Arg Ser Tyr Asp Tyr Ser Arg Arg Asn  (SEQ ID NO. 3)
                           5                   10                  15

           Val Arg Lys Asn
           20

(4) SfHA   Gly Ser Ser Gly Phe Gly Pro Tyr Val Ala His Gly Gly Tyr Ser Gly Tyr Glu Tyr  (SEQ ID NO. 4)
                           5                   10                  15

           Ala Trp Ser Ser Glu Ser Asp Phe Gly Thr
           20                  25

(5) AfH1   Tyr Gly Trp Gly Asp Gly Gly Tyr Gly Ser Asp Ser                        (SEQ ID NO. 5)
                           5                   10
```

-continued

```
(6) AfH5   Asp Glu Tyr Val Asp Asn                                             (SEQ ID NO. 6)
                           5

(7) AfH6   Val Glu Thr Ile Val Leu Glu Glu Asp Pro Tyr Gly His Glu Asp Ile Tyr Glu Glu  (SEQ ID NO. 7)
                           5                   10                  15

           Asp
           20

(8) AfH7   Asp Asp Gly Phe Val Leu Asp Gly Gly Tyr Asp Ser Glu                 (SEQ ID NO. 8)
                           5                   10
```

Still further, a third aspect (3) provides a peptide excellent for promoting cell growth containing any of the following amino acid sequences from (1) to (8):

```
(1) A-6-2  Val Ile Thr Thr Asp Ser Asp Gly Asn Glu                             (SEQ ID NO. 1)
                           5                   10

(2) A-6-6  Asn Ile Asn Asp Phe Asp Glu Asp                                     (SEQ ID NO. 2)
                           5

(3) SfHe   Ala Ala Ser Ser Val Ser Ser Ala Ser Ser Arg Ser Tyr Asp Tyr Ser Arg Arg Asn  (SEQ ID NO. 3)
                           5                   10                  15

           Val Arg Lys Asn
           20

(4) SfHA   Gly Ser Ser Gly Phe Gly Pro Tyr Val Ala His Gly Gly Tyr Ser Gly Tyr Glu Tyr  (SEQ ID NO. 4)
                           5                   10                  15

           Ala Trp Ser Ser Glu Ser Asp Phe Gly Thr
           20                  25

(5) AfH1   Tyr Gly Trp Gly Asp Gly Gly Tyr Gly Ser Asp Ser                     (SEQ ID NO. 5)
                           5                   10

(6) AfH5   Asp Glu Tyr Val Asp Asn                                             (SEQ ID NO. 6)
                           5

(7) AfH6   Val Glu Thr Ile Val Leu Glu Glu Asp Pro Tyr Gly His Glu Asp Ile Tyr Glu Glu  (SEQ ID NO. 7)
                           5                   10                  15

           Asp
           20

(8) AfH7   Asp Asp Gly Phe Val Leu Asp Gly Gly Tyr Asp Ser Glu                 (SEQ ID NO. 8)
                           5                   10
```

Still further, a fourth aspect (4) provides a method of separating and obtaining peptides which are excellent in promoting cell growth from the noncrystalline portions by hydrolysis of undegraded silk protein from a domesticated silkworm or degraded silk fibroin from a wild silkworm belonging to the genus *Antheraea*, and by subsequent molecular fractionation.

Still further, a fifth aspect (5) provides a method of separating and obtaining peptides which are excellent in promoting cell growth from the noncrystalline portions in the above fourth invention wherein the hydrolysis is conducted by using a dilute acid, hydroxylamine or a protease.

Still further, sixth (6) and seventh (7) aspects provide a cell growth-promoting agent containing the peptide compositions described in the above (1) and (2) and the peptides described in the above (3).

Still further, eighth (8) and ninth (9) aspects provide a cell adhesion agent containing the peptide compositions described in the above (1) and (2) and the peptides described in the above (3).

Still further, tenth (10) and eleventh (11) aspects provide a wound healing promoting agent containing the peptide compositions described in the above (1) and (2) and the peptides described in the above (3).

Still further, twelfth (12) and thirteenth (13) aspects provide a cosmetic material containing the peptide compositions described in the above (1) and (2) and the peptides described in the above (3).

Still further, fourteenth (14) and fifteenth (15) aspects provide a cell culture substrate containing the peptide compositions described in the above (1) and (2) and the peptides described in the above (3).

This invention has succeeded in providing novel peptides which are excellent in cell growth and have specific amino acid sequences of molecular weights lower than 10,000, preferably ranging from 4,000 to 400, by separating and fractionating peptides from the noncrystalline portions of silk protein as well as by synthesizing peptides similar to such peptides.

These peptides may be used as biomaterials such as a cell adhesion agent, cell growth-promoting agent, wound healing promoting agent, material for skin care, like a cosmetic, etc., and cell culture substrate.

DESCRIPTION OF THE PREFERRED EMBODIMENTS

The peptides from the noncrystalline portions of silk protein which are excellent in promoting cell growth and the peptide compositions thereof have been obtained by the following procedures and also been determined for their amino acid sequences.

(1) Cocoon layer from a wild silkworm belonging to the genus *Antheraea*, such as domesticated silkworm or *Antheraea yamamai*, is degummed, then solubilized in an aqueous solution of LiSCN and centrifuged. The separated supernatant is recovered and dialyzed against water. The dialyzate is again centrifuged and the separated supernatant is recovered.
(2) To the purified supernatant which has been separated and recovered, a protease such as chymotrypsin is added and treated for hydrolysis.
(3) The supernatant (noncrystalline portion) of the solution after the hydrolysis treatment is separated from the precipitate layer (crystalline portion) and recovered.
(4) The supernatant (noncrystalline portion) is fractionated by reverse phase chromatography.
(5) Each fraction fractionated by the reverse phase chromatography is subjected to cell culturing.
(6) The fraction which is excellent in cell growth is fractionated by molecular weight by means of gel filtration chromatography, and fractions (peptide chains) having a cell growth rate 2-fold higher than that of a control fraction are determined for their amino acid sequences.
(7) Peptides expected to show excellent cell growth promotion are designed and synthesized based on the obtained peptide.

Thus, the present invention can allow separation and fractionation of peptides of molecular weights lower than 10,000, preferably ranging from 4,000 to 400, having excellent cell growth-promoting activity from the noncrystalline portions of silk protein, synthesis of peptides analogous to such peptides, and provision of these peptides as biomaterials, such as cell adhesion agents, cell growth-promoting agents, wound healing promoting agents, materials for skin care like cosmetics, etc., and cell culture substrates.

The cell growth-promoting peptides originating from silk protein of the present invention mean the peptides which show a cell growth rate 2-fold higher than that of a control in which cells are cultured in the absence of an added peptide in the three-day cell culture test as described in Examples 1 to 3.

Primary Structure of Fibroin from Domesticated Silkworm

In the case of domesticated silkworm, the silkworm spins silk protein at the time of spinning to spin a cocoon (composed of cocoon filament and a pupa). In the cocoon filament, there exist fibroin at its center and sericin at its periphery, and their existing ratio is known to be 70 to 80% (fibroin) to 20 to 30% (sericin).

Fibroin in cocoon filament (silk protein refers to a combination of fibroin and sericin or each individually) is ca. 370,000 in its molecular weight.

(Tasiro Yutaka and Otsuki Eiichi, Journal of Cell Biology, Vol, 46, P1 (1970)) (See non-patent literature 3)

In fibroin having a molecular weight of ca. 370,000, molecules having a size of ca. 350,000 (H-chain) and a size of ca. 25,000 (L-chain) are bound to each other via an S—S bond.

The fibroin H-chain has a very high molecular weight, while it is composed of repeating analogous sequences of amino acid residues.

According to Gen Bank accession no. AF 226688, the precursor protein of the H-chain is composed of the N-terminal portion (I), the repetitive part of a crystalline portion (R) and a noncrystalline portion (A), and the C-terminal portion (a).

The repetitive part is repeated by twelve crystalline portions (from R01 to R12) through the mediation of eleven noncrystalline portions (from A01 to A11) therebetween.

The crystalline portions are composed of a long repetition of a highly crystalline dipeptide (Gly-X). X is highly crystalline Ala or additionally Ser as the main component, and other minor components thereof include Tyr, Val, and the like.

In particular, the repetition of Gly Ala Gly Ala Gly Ser or Gly Ala is abundant.

As the result, the sum of Gly and Ala in the crystalline portion exceeds 50% and amounts to more than ca. 70%.

The peptides of A01 to A11 in the noncrystalline portions are similar to one another in their amino acid sequences, while small differences are found in each amino acid sequence.

Further, the sum of Gly and Ala in each noncrystalline portion (from A01 to A11) is less than 50%.

The N-terminal portion and the C-terminal portion are considered to be noncrystalline from their amino acid sequences and amino acid compositions, and similarly to A01 to A11, the sum of Gly and Ala is each less than 50%.

On the other hand, there exist some portions in which the sum of Gly and Ala exceeds 50% in partial peptides of ca. 6 to 10 residues within the noncrystalline portions.

<Precursor of Fibroin H-Chain>

I-R01A01R02A02R03A03R04A04R05A05R06A06R07A07R08A08R09A09R10A10R11A11R12-a

N-Terminal Portion: I

N-terminal portion (I) is the initial peptide portion and its amino acid sequence is as follows:

```
Met Arg Val Lys Thr Phe Val Ile Leu Cys Cys Ala Leu Gln     (SEQ ID NO. 9)
                5                   10

Tyr Val Ala Tyr Thr Asn Ala Asn Ile Asn Asp Phe Asp Glu
15                  20                  25

Asp Tyr Phe Gly Ser Asp Val Thr Val Gln Ser Ser Asn Thr
    30                  35                  40

Thr Asp Glu Ile Ile Arg Asp Ala Ser Gly Ala Val Ile Glu
        45                  50                  55
```

-continued

```
Glu Gln Ile Thr Thr Lys Lys Met Gln Arg Lys Asn Lys Asn
            60                  65                  70

His Gly Ile Leu Gly Lys Asn Glu Lys Met Ile Lys Thr Phe
                75                  80

Val Ile Thr Thr Asp Ser Asp Gly Asn Glu Ser Ile Val Glu
85                  90                  95

Glu Asp Val Leu Met Lys Thr Leu Ser Asp Gly Thr Val Ala
    100                 105                 110

Gln Ser Tyr Val Ala Ala Asp Ala Gly Ala Tyr Ser Gln Ser
        115                 120                 125

Gly Pro Tyr Val Ser Asn Ser Gly Tyr Ser Thr His Gln Gly
            130                 135                 140

Tyr Thr Ser Asp Phe Ser Thr Ser Ala Ala Val
                145                 150
```

Crystalline Portion: R01, R02, . . . , R12

All of R01, R02, . . . R12 are portions called crystalline portion, and the number of amino acid residues is more than 300 for each crystalline portion. It should be noted, however, that the number of amino acid residues of R12 is 54.

The sum of Gly and Ala in each of the crystalline portions (R01 to R11) exceeds ca. 70%.

Noncrystalline Portions: A01, A02, . . . , A11

They are composed of 28 to 32 amino acid residues and are called noncrystalline portion (A).

Their amino acid sequences are as follows:

```
A01  Gly Ser Ser Gly Phe Gly Pro Tyr Val Ala Asn Gly Gly Tyr Ser (SEQ ID NO. 10)
                     5                  10                  15

     Arg Ser Asp Gly Tyr Glu Tyr Ala Trp Ser Ser Asp Phe Gly Thr
                     20                 25                  30

A02  Gly Ser Ser Gly Phe Gly Pro Tyr Val Ala His Gly Gly Tyr Ser (SEQ ID NO. 11)
                     5                  10                  15

     Gly Tyr Glu Tyr Ala Trp Ser Ser Glu Ser Asp Phe Gly Thr
                     20                 25

A03  Gly Ser Ser Gly Phe Gly Pro Tyr Val Ala Asn Gly Gly Tyr Ser (SEQ ID NO. 12)
                     5                  10                  15

     Gly Tyr Glu Tyr Ala Trp Ser Ser Glu Ser Asp Phe Gly Thr
                     20                 25

A04  Gly Ser Ser Gly Phe Gly Pro Tyr Val Ala His Gly Gly Tyr Ser (SEQ ID NO. 13)
                     5                  10                  15

     Gly Tyr Glu Tyr Ala Trp Ser Ser Glu Ser Asp Phe Gly Thr
                     20                 25

A05  Gly Ser Ser Gly Phe Gly Pro Tyr Val Ala His Gly Gly Tyr Ser (SEQ ID NO. 14)
                     5                  10                  15

     Gly Tyr Glu Tyr Ala Trp Ser Ser Glu Ser Asp Phe Gly Thr
                     20                 25

A06  Gly Ser Ser Gly Phe Gly Pro Tyr Val Ala Asn Gly Gly Tyr Ser (SEQ ID NO. 15)
                     5                  10                  15

     Gly Tyr Glu Tyr Ala Trp Ser Ser Glu Ser Asp Phe Gly Thr
                     20                 25

A07  Gly Ser Ser Gly Phe Gly Pro Tyr Val Ala Asn Gly Gly Tyr Ser (SEQ ID NO. 16)
                     5                  10                  15

     Gly Tyr Glu Tyr Ala Trp Ser Ser Glu Ser Asp Phe Gly Thr
                     20                 25

A08  Gly Ser Ser Gly Phe Gly Pro Tyr Val Ala Asn Gly Gly Tyr Ser (SEQ ID NO. 17)
                     5                  10                  15
```

-continued

```
     Gly Tyr Glu Tyr Ala Trp Ser Ser Glu Ser Asp Phe Gly Thr
                     20                  25

A09  Gly Ser Ser Gly Phe Gly Pro Tyr Val Asn Gly Gly Tyr Ser     (SEQ ID NO. 19)
                     5                   10

     Gly Tyr Glu Tyr Ala Trp Ser Ser Glu Ser Asp Phe Gly Thr
     15                  20                  25

A10  Gly Ser Ser Gly Phe Gly Pro Tyr Val Ala Asn Gly Gly Tyr Ser (SEQ ID NO. 19)
                     5                   10                  15

     Gly Tyr Glu Tyr Ala Trp Ser Ser Glu Ser Asp Phe Gly Thr
                     20                  25

A11  Gly Ser Ser Gly Phe Gly Pro Tyr Val Ala Asn Gly Gly         (SEQ ID NO. 20)
                     5                   10

     Tyr Ser Arg Arg Glu Gly Tyr Glu Tyr Ala Trp Ser Ser
         15                  20                  25

     Lys Ser Asp Phe Glu Thr
                 30
```

C-Terminal Portion: a

The amino acid sequence of the noncrystalline portion on the C-terminal side is as follows:

```
Ala Ala Ser Ser Val Ser Ser Ala Ser Ser Arg Ser Tyr Asp Tyr (SEQ ID NO. 21)
                5                   10                  15

Ser Arg Arg Asn Val Arg Lys Asn Cys Gly Ile Pro Arg Arg Gln
                20                  25                  30

Leu Val Val Lys Phe Arg Ala Leu Pro Cys Val Asn Cys
                35                  40
```

For convenience and reference to understand the present invention, notation for amino acids or amino acid residues in protein, charge characteristics thereof and the like are described in the following Table 10.

TABLE 10

| 1 character | 3 character | Amino acid |
|---|---|---|
| A | Ala | alanine residues |
| C | Cys | cystine |
| D | Asp | aspartic acid |
| E | Glu | glutamic acid |
| F | Phe | phenylalanine |
| G | Gly | glycine |
| H | His | histidine |
| I | Ile | isoleucine |
| K | lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |

TABLE 10-continued

| 1 character | 3 character | Amino acid |
|---|---|---|
| V | Val | valine |
| W | Trp | tryptophan |
| Y | Tyr | tyrosine |

Based on the side chain characteristics, amino acids are classified as four groups consisting of acidic amino acid, polar non-charged amino acid, non-polar amino acid and basic amino acid (1) Acidic amino acid: Glu, Asp (2) Polar non-charged amino acid: Asn, Ser, Gln, Tyr, Thr, Cys, Phe (3) Non-polar amino acid: Ala, Gly, Val, Pro, Leu, Ile, Trp (4) Basic amino acid: His, Lys, Arg The fibroin L-chain shown below is a noncrystalline portion, when compared to the amino acid sequences of the crystalline portions and the noncrystalline portions of the fibroin H-chain.

<Amino Acid Sequence in Fibroin L-Chain>

```
Met Lys Pro Ile Phe Leu Val Leu Leu Val Ala Thr Ser Ala     (SEQ ID NO. 22)
                5                   10

Tyr Ala Ala Pro Ser Val Thr Ile Asn Gln Tyr Ser Asp Asn
15                  20                  25
```

-continued

```
Glu Ile Pro Arg Asp Ile Asp Asp Gly Lys Ala Ser Ser Val
    30                  35                  40

Ile Ser Arg Ala Trp Asp Tyr Val Asp Asp Thr Asp Lys Ser
        45                  50                  55

Ile Ala Ile Leu Asn Val Gln Glu Ile Leu Lys Asp Met Ala
            60                  65                  70

Ser Gln Gly Asp Tyr Ala Ser Gln Ala Ser Ser Val Ala Gln
                75                  80

Thr Ala Gly Ile Ile Ala His Leu Ser Ala Gly Ile Pro Gly
85                  90                  95

Asp Ala Cys Ala Ala Ala Asn Val Ile Asn Ser Tyr Thr Asp
    100                 105                 110

Gly Val Arg Ser Gly Asn Phe Ala Gly Phe Arg Gln Ser Leu
        115                 120                 125

Gly Pro Phe Phe Gly His Val Gly Gln Asn Leu Asn Leu Ile
            130                 135                 140

Asn Gln Leu Val Ile Asn Pro Gly Gln Leu Arg Tyr Ser Val
                145                 150

Gly Pro Ala Leu Gly Cys Ala Gly Gly Gly Arg Ile Tyr Asp
155                 160                 165

Phe Glu Ala Ala Trp Asp Ala Ile Leu Ala Ser Ser Asp Ser
    170                 175                 180

Ser Phe Leu Asn Glu Glu Tyr Cys Ile Val Lys Arg Leu Tyr
        185                 190                 195

Asn Ser Arg Asn Ser Gln Ser Asn Asn Ile Ala Ala Tyr Ile
            200                 205                 210

Thr Ala His Leu Leu Pro Pro Val Ala Gln Val Phe His Gln
                215                 220

Ser Ala Gly Ser Ile Thr Asp Leu Leu Arg Gly Val Gly Asn
225                 230                 235

Gly Asn Asp Ala Thr Gly Leu Val Ala Asn Ala Gln Arg Tyr
    240                 245                 250

Ile Ala Gln Ala Ala Ser Gln Val His Val
        255                 260
```

On the other hand, the amino acid sequence of silk protein from the wild silkworm is different from that of the domesticated silkworm, while wild silkworms belonging to the genus *Antheraea* such as *Antheraea yamamai, Antheraea pernyi, Samia cynthia ricini, Antheraea assama* and *Antheraea mylitta* have almost identical amino acid sequences.

For fibroin of *Antheraea yamamai*, the portion consisting of a repetition of 10 or more alanine residues (A) alone is referred to crystalline portion, and the other portions besides this are referred to noncrystalline portion.

Compared to fibroin from the domesticated silkworm, fibroin from the wild silkworm belonging to the genus *Antheraea* has a smaller number of residues in each repetitive part of the crystalline portion and the noncrystalline portion.

The amino acid sequences of the noncrystalline portions of fibroin from *Antheraea yamamai* excepting the crystalline portions having 10 or more sequential alanine residues are shown below.

From the amino acid compositions, the N-terminal portion and the C-terminal portion are also noncrystalline portions.

<Primary Structure of Noncrystalline Portions of Fibroin from *Antheraea yamamai*>

```
N-terminal portion: initial peptide                 (SEQ ID NO. 23)

Met Arg Val Thr Ala Phe Val Ile Leu Cys Cys Ala Leu Gln
                5                   10

Tyr Ala Thr Ala Asn Asn Leu His His His Asp Glu Tyr Val
15                  20                  25
```

-continued

```
Asp Asn His Gly Gln Leu Val Glu Arg Phe Thr Thr Arg Lys
    30                  35                  40

His Tyr Glu Arg Asn Ala Ala Thr Arg Pro His Leu Ser Gly
        45                  50                  55

Asn Glu Arg Leu Val Glu Thr Ile Val Leu Glu Glu Asp Pro
            60                  65                  70

Tyr Gly His Glu Asp Ile Tyr Glu Glu Asp Val Val Ile Asn
                75                  80

Arg Val Pro Gly Ala Ser Ser Ser Ala Ala Ala Ala Ser Ser
85                  90                  95

Ala Ser Ala Gly Ser Gly Gln Thr Ile Ile Val Glu Arg Gln
    100                 105                 110

Ala Ser His Gly Ala Gly Gly Ala
        115                 120
```

<u>Noncrystalline portions:</u>

```
Ala Gly Ala Ala Ala Gly Ala Ala Ala Gly Ser Ser Ala Arg    (SEQ ID NO. 24)
                5                   10

Gly Gly
15

Ser Gly Phe Tyr Glu Thr His Asp Ser Tyr Ser Ser Tyr Gly    (SEQ ID NO. 25)
                5                   10

Ser Gly Ser Ser Ser Ala Ala Ala Ala Ser Ser Gly Ala Gly
15                  20                  25

Gly Ala Gly Gly Gly Tyr Gly Trp Gly Asp Gly Gly Tyr Gly
    30                  35                  40

Ser Asp Ser
        45

Gly Ser Gly Ala Gly Gly Arg Gly Asp Gly Gly Tyr Gly Ser    (SEQ ID NO. 26)
                5                   10

Gly Ser Ser
15

Arg Arg Ala Gly His Asp His Ala Ala Gly Ser Ser Gly Gly    (SEQ ID NO. 27)
                5                   10

Gly Tyr Ser Trp Asp Tyr Ser Ser Tyr Gly Ser Glu Ser
15                  20                  25

Gly Ser Gly Ala Gly Gly Val Gly Gly Gly Tyr Gly Gly Gly    (SEQ ID NO. 28)
                5                   10

Asp Gly Gly Tyr Gly Ser Gly Ser Ser
15                  20

Arg Arg Ala Gly His Asp Arg Ala Ala Gly Ser                (SEQ ID NO. 29)
                5                   10

Ser Gly Ala Gly Gly Ser Gly Gly Gly Tyr Gly Trp Gly Asp    (SEQ ID NO. 30)
                5                   10

Gly Gly Tyr Gly Ser Asp Ser
15                  20

Gly Ser Gly Ala Gly Arg Ala Gly                            (SEQ ID NO. 31)
                5

Gly Asp Tyr Gly Trp Gly Asp Gly Gly Tyr Gly Ser Asp Ser    (SEQ ID NO. 32)
                5                   10

Arg Gln Ala Gly His Glu Arg Ala Ala Gly Ser                (SEQ ID NO. 33)
                5                   10

Ser Gly Ala Gly Gly Ser Gly Arg Gly Tyr Gly Trp Gly Asp    (SEQ ID NO. 34)
                5                   10
```

-continued

Gly Gly Tyr Gly Ser Asp Ser
15 20

Gly Ser Gly Ala Gly Gly Ala Gly Gly Asp Tyr Gly Trp Gly (SEQ ID NO. 35)
5 10

Asp Gly Gly Tyr Gly Ser Asp
15 20

Gly Ser Gly Ala Gly Gly Ala Gly Gly Asp Tyr Gly Trp Gly (SEQ ID NO. 36)
5 10

Asp Gly Gly Tyr Gly Ser Asp Ser
15 20

Ser Gly Ala Gly Gly Ala Gly Gly Gly Tyr Gly Trp Gly Asp (SEQ ID NO. 37)
5 10

Gly Gly Tyr Gly Ser Asp Ser
15 20

Ser Gly Ala Gly Gly Ala Gly Gly Tyr Gly Gly Tyr Gly Ser (SEQ ID NO. 38)
5 10

Asp Ser
15

Ser Gly Ala Gly Gly Ser Gly Gly Gly Tyr Gly Trp Gly Asp (SEQ ID NO. 39)
5 10

Gly Gly Tyr Gly Ser Gly Ser
15 20

Gly Ser Gly Ala Gly Gly Val Gly Gly Gly Tyr Gly Trp Gly (SEQ ID NO. 40)
5 10

Asp Gly Gly Tyr Gly Ser Asp Ser
15 20

Ser Gly Ala Gly Gly Arg Gly Asp Gly Gly Tyr Gly Ser Gly (SEQ ID NO. 41)
5 10

Ser Ser
15

Gly Ser Gly Ala Gly Gly Ala Gly Gly Gly Tyr Gly Trp Gly (SEQ ID NO. 42)
5 10

Asp Gly Gly Tyr Gly Ser Asp Ser
15 20

Arg Arg Ala Gly His Asp Arg Ala Ala Gly Cys (SEQ ID NO. 43)
5 10

Ser Gly Ala Gly Gly Thr Gly Gly Gly Tyr Gly Trp Gly Asp (SEQ ID NO. 44)
5 10

Gly Gly Tyr Gly Ser Asp Ser
15 20

Ser Gly Ala Gly Gly Ser Gly Gly Gly Tyr Gly Trp Gly Asp (SEQ ID NO. 45)
5 10

Gly Gly Tyr Gly Ser Asn Ser
15 20

Ser Gly Ala Gly Arg Ser Gly Gly Gly Tyr Gly Trp Gly Asp (SEQ ID NO. 46)
5 10

Gly Gly Tyr Ser Ser Asp Ser
15 20

Ser Gly Ala Gly Gly Ser Gly Gly Tyr Gly Gly Tyr Gly Ser (SEQ ID NO. 47)
5 10

Asp Ser
15

-continued

```
Gly Ser Gly Ala Gly Gly Val Gly Gly Gly Tyr Gly Trp Gly    (SEQ ID NO. 48)
                5                   10

Asp Gly Gly Tyr Gly Gly Tyr Gly Ser Asp Ser
15                  20                  25

Gly Ser Gly Ala Gly Gly Val Gly Gly Gly Tyr Gly Arg Gly    (SEQ ID NO. 49)
                5                   10

Asp Ser Gly Tyr Gly Ser Gly Ser Ser
15                  20

Gly His Gly Arg Ser Ser Gly Ser                            (SEQ ID NO. 50)
                5

Ser Gly Ala Gly Gly Ser Gly Gly Gly Tyr Gly Trp Asp Tyr    (SEQ ID NO. 51)
                5                   10

Gly Ser Tyr Gly Ser Asp Ser
15                  20

Ser Ser Gly Ala Gly Gly Ser Gly Gly Gly Tyr Gly Trp Asp    (SEQ ID NO. 52)
                5                   10

Tyr Gly Gly Tyr Gly Ser Asp Ser
15                  20

Gly Ser Gly Ala Gly Gly Ser Gly Gly Gly Tyr Gly Trp Gly    (SEQ ID NO. 53)
                5                   10

Asp Gly Gly Tyr Gly Ser Asp Ser
15                  20

Ser Arg Arg Ala Gly His Asp Arg Ala Tyr Gly Ala Gly Ser    (SEQ ID NO. 54)
                5                   10

Gly Ala Gly Ala Ser Arg Pro Val Gly Ile Tyr Gly Thr Asp    (SEQ ID NO. 55)
                5                   10

Asp Gly Phe Val Leu Asp Gly Gly Tyr Asp Ser Glu Gly Ser
15                  20                  25
```

C-terminal portion:

```
Ser Ser Ser Gly Arg Ser Thr Glu Gly His Pro Leu Leu Ser    (SEQ ID NO. 56)
                5                   10

Ile Cys Cys Arg Pro Cys Ser His Arg His Ser Tyr Glu Ala
15                  20                  25

Ser Arg Ile Ser Val His
    30
```

As to silk protein components excellent in promoting cell growth, an analysis was performed on which portion of each component is responsible for cell growth promotion in the present invention, disclosing that it was associated with the noncrystalline portions.

The noncrystalline portions of fibroin mean the portions having the amino acid sequences described above.

Accordingly, the N-terminal portion and the C-terminal portion are contained in the noncrystalline portions.

All of A01 to A11 (peptides of 28 to 32 residues) of the noncrystalline portions from the domesticated silkworm show similar excellent cell growth promotion, while the amino acid sequences of A01 to A11 are not identical.

The sequence of amino acid residues of A11 differs from that of each of other A01 to A10 within 8 residues out of its 32 residues.

Accordingly, even if there is ca. 30% or less difference in the sequence of amino acid residues, the cell growth-promoting activity is not influenced.

Even if there is an increase/decrease in the number of amino acid residues within ca. 20%, the cell growth promoting-activity is not influenced.

However, it is preferred that the difference in the amino acid sequences is less than 50% to retain the cell growth-promoting activity.

On the other hand, peptides having a very small number of amino acid residues may not express the cell growth-promoting activity.

Particularly when the number of amino acid residues is not more than two, the cell growth may be inhibited.

Therefore, peptides for the cell growth promotion are better to be peptides of from 4 to 40 residues, preferably from 6 to 32 residues.

Further, it was found that a partial peptide containing more acidic amino acid residues and/or polar non-charged amino acid residues and few basic amino acid residues in the noncrystalline portions is better for the cell growth promotion.

Particularly, acidic amino acid residues showed an excellent cell-growth promoting activity.

The noncrystalline portions show an excellent growth-promoting activity as a whole, whereas there exist, as a part, some sequence portions of amino acids showing a low growth-promoting activity because the sum of Gly and Ala exceeds 55% and also abundant basic amino acids are contained.

Accordingly, partial peptides in which acidic amino acids and/or polar non-charged amino acids are present and basic amino acids are hardly present and are separated and recovered from the noncrystalline portions of fibroin.

Among the recovered partial peptides, the peptides having 40 or less amino acid residues and showing a value of cell growth rate two fold higher than that of a control in which there is no added peptide in the cell culture test described in Examples 1 to 3 are designated as SDFGP.

A mixture of a plurality of peptides having 4 to 40 amino acid residues is also designated as SDFGP, as long as its cell growth rate shows 2-fold or higher activity than that of the control.

For the above conditions, a partial peptide from the noncrystalline portions is required to fulfill the following items, which is readily inferred from the results shown in Table 6:

(1) The sum of the numbers of Gly and Ala relative to the total number of amino acid residues in a peptide is not higher than 55%. This is because a higher content of Gly and Ala is liable to form a crystal.

(2) The number of basic amino acid residues relative to the total number of amino acid residues in a peptide is not more than 25%.

(3) There exist acidic amino acids and/or polar non-charged amino acids.

When these conditions are not met, the cell growth may be inhibited.

In this connection, the properties of amino acids or peptides differ by the chemical structures of their side chains.

Although acidic amino acids are excellent for cell growth promotion, the length of the side chain differs between Glu and Asp, and thus, flexibility or conformation of the side chain and principal chain differs between them, thus contributing to dissimilar cell growth promotion.

Likewise, this is true for various amino acids referred to as polar non-charged amino acids or basic amino acids, and due to variations in physicochemical properties, the same cell promoting and cell inhibiting activities are not always exerted.

Cells forming our body are largely divided into adherent cells and floating cells.

The adherent cells include skin cells, vascular cells, gland cells, and the like. The floating cells include blood cells and the like.

The growth process of adherent cells starts with adhesion and then proliferation, and thus may be roughly divided into adhesion and proliferation.

SDFGP of the present invention has a property of supporting both adherence and proliferation, and is relatively better for adherence when compared between them.

Being better for proliferation gives rise to abnormal proliferation of cells, and may be associated with a safety issue for prolonged use.

Accordingly, SDFGP of the present invention which is good for adherence, has proliferation promotion, and does not inhibit cell growth is excellent for skin care materials and biomaterials.

When partial peptides are separated and recovered from silk protein in practice, silk protein is cleaved with a protease that cleaves specific peptide bonds or otherwise with a chemical serving the same purpose, and then, peptides that are formed of not more than 40 amino acid residues and belong to the noncrystalline portions are recovered.

In addition, it is also possible to design a peptide excellent for cell growth on the basis of the obtained peptides and then synthesize the peptide.

1. Separation and Recovery of Peptides from Silk Protein

In order to separate and recover the noncrystalline portions of silk protein, a characteristic of the noncrystalline portions may be used.

Since the noncrystalline portions are readily soluble in water, a silk material may be immersed in near neutral water (pH 5.0 to 9.0).

However, peptides of the noncrystalline portions cannot be efficiently obtained merely by the immersion of the silk material.

Hence, specific peptide bonds of silk protein are actively cleaved.

Such a cleavage method of peptide bonds preferably employs a chemical substance, an enzyme or the like which actively cleaves specific peptide bonds.

This is described below.

1) Raw Material

For the domesticated silkworm, raw material used is silk protein with fibroin H-chain, L-chain and remaining sericin a component.

For the wild silkworm (e.g., *Antheraea yamamai, Antheraea pernyi, Samia cynthia ricini, Antheraea assama* and *Antheraea mylitta*, and the like), raw material used is the one in which a band of the fibroin is observed on an electrophoretogram as clearly as that of the fibroin H-chain from the domesticated silkworm.

The raw material may be individually fibroin and sericin, or those existing together.

Thus, the raw material for the present invention may include all of cocoon filaments, raw silk, silk fabrics and knits, silk threads (fibroin fiber), remaining threads thereof or fibers, powder, film and the like with the use thereof as a raw material, and protein fiber material (silk material) spun by silkworm species such as domesticated silkworm and wild silkworm.

It should be noted that these materials have to contain the fibroin H-chain and sericin a component of domesticated silkworm and their corresponding components of wild silkworm.

Since the fibroin H-chain is more vulnerable to degradation than its L-chain, a partially remaining H-chain indicates that the L-chain is mostly left undegraded.

2) Solubilization of the Material

The material of the above 1) to be solubilized by a neutral salt may be a degummed material, half-degummed material, undegummed material, or an intermediate material thereof.

It may be sericin fiber from silkworm cocoon.

An important point is that their silk protein is not degraded or the fibroin H-chain, the a component of sericin and their corresponding proteins remain partially undegraded after various processing steps.

Whether the H-chain, the a component and the like remain or not is confirmed by the presence of their respective corresponding bands on an electrophoretogram.

The neutral salt to be used as a solubilizer for raw silk threads includes, for example, calcium chloride, copper ethylenediamine, sodium thiocyanate, lithium thiocyanate, lithium bromide, magnesium nitrate, and the like.

The neutral salt is preferably in an aqueous saturated solution or at a concentration not less than 50% saturation [weight (g)/volume (ml)].

In the case where fibroin and sericin are contained, for example, cocoon filaments, undegummed material, half-degummed material, and the like are solubilized using the above neutral salt in a manner similar to that for silk threads.

On the other hand, when sericin occupies 98% or more, as in the case of sericin fiber from silkworm cocoon, the solubilization is carried out with 8 M urea within 10 min at 70 to 90 degrees C.

Moreover, sericin fiber from silkworm cocoon may be solubilized with 9 M LiBr within 30 min at room temperature (20 to 30 degrees C.).

The conditions for solubilization may be varied according to the above conditions.

At the step of solubilizing the silk material in a neutral salt solution, an alcohol such as methyl alcohol, ethyl alcohol and propyl alcohol may be added to the neutral salt.

When calcium chloride is used as the neutral salt, the solubilization is carried out at a temperature not higher than 94 degrees C., preferably in the range of from 75 to 85 degrees C.

When lithium bromide is used, the raw material is solubilized at a temperature lower than ca. 50 degrees C. Thus, depending on the neutral salt used, the conditions for solubilization vary, and a method in which the fibroin H-chain and the a component of sericin may remain or its corresponding method is employed for solubilization.

During solubilizing silk material, (1) the solubilization may be accelerated by stirring.

(2) the solubilization is difficult at a lower temperature.

Although a higher temperature may facilitate the solubilization, a vigorous lowering in molecular weight may take place.

The solution in which silk is solubilized with a neutral salt contains the neutral salt, alcohol, and so on besides fibroin or a mixture of fibroin and sericin.

From this solution, insoluble materials are first removed, and then low molecular weight compounds having a molecular weight lower than 5,000 are removed using a dialysis membrane or a dialysis equipment.

A solution of silk protein is obtained by such dialysis.

3) Degradation by Enzyme and Recovery

In general, it is said that cleavage of protein with a protease takes place at specific peptide bonds, and that modifications of the side chains of amino acid residues tend not to occur since its cleavage is carried out under a mild condition.

Furthermore, complicated fragmentation arising from nonspecific cleavage of protein may be avoided.

Such enzymes include lysyl endopeptidase, arginyl endopeptidase, chymotrypsin, papain, pepsin, rennin, pancreatin, elastase and the like.

When a protease is added to an aqueous solution of silk protein, the silk protein is cleaved between specific peptide bonds.

Among these, chymotrypsin is particularly preferred to separate the crystalline and noncrystalline portions.

When the cleaved peptides from silk protein are mainly composed of fragments generated from the crystalline portions of silk protein, these are prone to aggregate, and precipitate upon aggregation (coagulation or crystallization).

Even if their aggregation hardly occurs, peptides originating from the crystalline portion tend to aggregate more readily, and the addition of alcohol (methyl alcohol, ethyl alcohol, etc.) and the like as a coagulant triggers aggregation beginning from the peptides derived from the crystalline portions, and they precipitate out.

After removal of the precipitate, the remainder is a solution of peptides from the noncrystalline portions.

For the removal of the precipitate, the solution containing the precipitate is centrifuged (1,000 to 10,000 G) to remove it.

The solution freed of the precipitate is an aqueous solution of peptides, originating from the noncrystalline portions, which have been split off from the noncrystalline portions.

Upon drying this solution, film-like or powder-like peptides are obtained.

It should be noted that, when alcohol is added to the aqueous solution of peptides generated from the noncrystalline portions, the peptides from the noncrystalline portions start to aggregate in turn and precipitate out as the alcohol concentration becomes higher.

The peptides from the noncrystalline portions may contain partial peptides from the crystalline portions as long as the latter are within ca. 50%.

However, to obtain peptides excellent for promoting cell growth, the sum of glycine and alanine residues are preferred not to exceed 55%, even if the peptides are those from the noncrystalline portions.

Further, the number of basic amino acid residues is preferred not to be higher than 25% of that of the residues constituting the peptide.

On the other hand, larger numbers of acidic amino acid residues and non-polar charged amino acid residues are preferred.

Particularly, a larger number of acidic amino acid residues is better for cell growth promotion.

The drying is carried out by lyophilization or spray drying.

Even if the peptides from the noncrystalline portions are crystallized after drying, they are readily soluble in water owing to their lower molecular weights.

2. Synthesis of Fibroblast Growth-Promoting Peptide (SDFGP) from Silk Protein

The SDFGP separated and recovered from silk protein includes the following peptides:

These are merely examples of SDFGP.

Further, it goes without saying that there are many SDFGP satisfying the conditions described above.

```
A-6-2     Val Ile Thr Thr Asp Ser Asp Gly Asn Glu   (SEQ ID NO. 1)
                          5                   10

A-6-6     Asn Ile Asn Asp Phe Asp Glu Asp           (SEQ ID NO. 2)
                          5
```

-continued

```
SfHe    Ala Ala Ser Ser Val Ser Ser Ala Ser Ser   (SEQ ID NO. 3)
                        5                   10

        Arg Ser Tyr Asp Tyr Ser Arg Arg Asn Val
                        15                  20

        Arg Lys Asn

SfHA    Gly Ser Ser Gly Phe Gly Pro Tyr Val Ala   (SEQ ID NO. 4)
                        5                   10

        His Gly Gly Tyr Ser Gly Tyr Glu Tyr Ala
                        15                  20

        Trp Ser Ser Glu Ser Asp Phe Gly Thr
                        25

AfH1    Tyr Gly Trp Gly Asp Gly Gly Tyr Gly Ser   (SEQ ID NO. 5)
                        5                   10

        Asp Ser

AfH5    Asp Glu Tyr Val Asp Asn                   (SEQ ID NO. 6)
                        5

AfH6    Val Glu Thr Ile Val Leu Glu Glu Asp Pro   (SEQ ID NO. 7)
                        5                   10

        Tyr Gly His Glu Asp Ile Tyr Glu Glu Asp
                        15                  20

AfH7    Asp Asp Gly Phe Val Leu Asp Gly Gly Tyr   (SEQ ID NO. 8)
                        5                   10

        Asp Ser Glu
```

Even only a portion of the amino acid sequences of these SDFGP may serve as SDFGP showing excellent cell-growth promotion.

Further, these peptides may be repeated within 40 residues or connected to other peptides.

However, a single amino acid state is not endowed with the cell growth-promoting function.

The number of amino acid residues required for cell growth-promoting function is not less than 4 residues.

On the other hand, its preferred number is 40 or less in view of the efficiency of peptide synthesis.

The synthesis of SDFGP mimics the amino acid sequences of the noncrystalline portions of silk protein, and the peptides which satisfy the conditions described above are synthesized.

The number of amino acid residues of a synthetic peptide is from 4 to 40, preferably from 6 to 32.

In this case, its amino acid sequence is not necessarily the same as that of silk protein.

For example, the amino acid sequences of the noncrystalline portions (A0 to A11) of the fibroin H-chain are not totally identical, while their growth promoting-activities are approximately the same, and all of them conform to SDFGP.

Accordingly, its amino acid sequence may differ about 30% or less, preferably differ 50% or less.

In this case, a larger number of acidic amino acids is better, and the presence of polar non-charged amino acids is preferred.

In contrast, the absence of basic amino acids is preferred.

In other words, the amino acid residues in each SDFGP may be replaced with other amino acid residues.

In this case, the number of basic amino acid residues is designed so as to become 25% or less of that constituting the peptide.

On the other hand, a larger number of acidic amino acids in a peptide (SDFGP) is preferred.

The whole amino acid residues may be composed of acidic amino acids and/or polar non-charged amino acids.

Thus, Asp Ser Asp Gly Asp Glu (SEQ ID NO. 70) from A-6-2, Asp Glu Asp Glu Asp Glu (SEQ ID NO. 71) and Glu Asp Glu Asp Glu Asp (SEQ ID NO. 72) from A-6-6, Ser Ser Glu Ser Ser Glu (SEQ ID NO. 73) and Tyr Gly Gly Tyr Glu Tyr (SEQ ID NO. 74) from SfHA, Asp Gly Gly Tyr Gly Gly Asp (SEQ ID NO. 75) from AfH 1, Asp Glu Tyr Asp Glu Tyr (SEQ ID NO. 76) from AfHS, Tyr Glu Glu Asp Tyr Glu Glu Asp (SEQ ID NO. 77) from AfHG, and the like, and further many more peptides such as Glu Glu Glu Glu (SEQ ID NO. 78), Glu Glu Glu Glu Glu Glu (SEQ ID NO. 79), Glu Tyr Glu Tyr Glu Tyr (SEQ ID NO. 80), Glu Glu Tyr Glu Glu Tyr (SEQ ID NO. 81), Tyr Tyr Tyr Tyr Tyr Tyr (SEQ ID NO. 82), Glu Gly Ser Glu Gly Ser (SEQ ID NO. 83) may become SDFGP.

It goes without saying that these peptides may be repeated or connected to other peptides as long as they are in the range of the conditions described above and have a molecular weight of 10,000 or less, preferably in the range of 4,000 to 400. In addition, the amino residues may be replaced with other amino acid residues.

4. Use

The peptide sets obtained from the noncrystalline portions of silk protein and SDFGP are not only excellent for cell growth promotion but also easily water-soluble.

Further, their molecular weights are approximately lower than 4,000, and therefore their forms are stable in a dissolved state for a prolonged period.

Still further, mixing various SDFGP may promote higher cell growth compared to a single SDFGP.

Therefore, a mixture of these is added to cell culture medium, lotion, milky lotion, cream, ointment, instillation, food, and the like.

Since the peptide sets and SDFGP of the present invention are excellent for promoting skin cell growth, they are excellent materials for skin care, cell culture, and further for improvements in other fields besides the above, for example, clothing fibers, cosmetic powders, resins, etc.

EXAMPLE 1

Cell Growth Activity of Enzymic Digests of Silk Fibroin (1) Enzymic Degradation of the Noncrystalline Portions of Silk Fibroin, and Subsequent Separation and Fractionation Cocoons of a domesticated silkworm were cut open to remove pupae, and cocoon layers (10 g) were immersed in 30 volumes of 8 M urea for 10 min at 90 degrees C. to extract sericin.

The residue after the extraction was washed with water, dried, and prepared as fibroin.

One g of fibroin was immersed in 10 ml of 9 M LiSCN to solubilize. To this, 10 ml of distilled water was added and centrifuged for 10 min at 3,000 rpm.

The supernatant was put into a semipermeable membrane tube and dialyzed against 50 volumes of water.

The dialysis was performed four times, changing the external dialysis water every 30 minutes.

After the dialysis, the solution was again centrifuged, and then 0.1 M sodium dihydrogenphosphate (pH 8.5) was added to adjust its pH to 7 to 8.

When chymotrypsin amounting to 1/100 of fibroin was added to that solution and left for 4 hours at 40 degrees C., precipitates were formed.

Proteins or peptides in the supernatant originating from the noncrystalline portion (A) of fibroin were designated as noncrystalline portion (A'), and proteins or peptides in the precipitates originating from the crystalline portion (C) were designated as crystalline portion (C').

The crystalline portion was washed with water, dissolved in 1 ml of 9 M LiSCN and dialyzed against 50 volumes of water using a semipermeable membrane tube as described above, and the amount of protein in the aqueous solution was determined.

The amount of protein in the supernatant was determined without any further treatment.

(2) Coating on Cell Culture Vessel

The concentrations of aqueous solutions of these crystalline portion (C') and noncrystalline portion (A') were each adjusted to 0.025% and 0.0025%, respectively, by adding 70% ethanol, and 1 ml each of the diluted solutions was put into dishes (35 mmϕ, Falcon) made of polystyrene and then air-dried.

Only 1 ml of 70% ethanol was added to dishes for control.

(3) Cell Culture

The cells used were human skin fibroblasts (originating from adult normal skin) purchased (frozen) from Sanko Junyaku Co., Ltd.

The culture medium used was the low serum culture medium for human skin fibroblast growth purchased from Kurabo Industries Ltd. (10 ml of LSGS (low serum growth supplement) added to 500 ml of Medium 106S (basal medium for skin fibroblast)).

It should be noted that LSGS has a cell growth-promoting activity.

The medium was added at 2 ml per dish, and 80,000 cells were inoculated and cultured for 3 days.

(4) Measurement of Viable Cell Number with Alamer Blue Dye

The medium at 2 ml per dish and Alamer Blue (Iwaki Glass Co.) at 0.1 ml per dish were added and cultured for 2 hours at 37 degrees C., and then the reduced amount of Alamer Blue dye calculated from the absorbances at 570 nm and 600 nm was correlated with viable cell number.

The growth of human skin fibroblasts in dishes coated with the crystalline portion and the noncrystalline portion compared to that of control (100%) having no silk protein component is shown in Table 1.

The cell growth rates in dishes coated with the silk protein components showed higher values in all cases compared to the control.

Particularly, the growth rate of the noncrystalline portion (C') at 0.025% concentration was high. This portion is a mixture of SDFGP.

The growth rate of the crystalline portion at a higher concentration (0.025%) was worse than that at a lower concentration (0.0025%).

This is considered to be due to an inhibition of the cell growth by silk protein of the crystalline portion.

EXAMPLE 2

Amino Acid Sequence of Cell Growth-Promoting Peptides

It was found in Example 1 that the noncrystalline portion of fibroin promoted the cell growth more actively than the crystalline portion thereof.

However, the noncrystalline portion fractionated in Example 1 is likely to be a mixture of peptides generated by the enzymic cleavage.

Hence, the noncrystalline portion was further separated to identify the site of cell growth promotion.

First, reverse phase chromatography was carried out to separate the peptides contained in the noncrystalline portion in Example 1 according to their differences in polarity.

The column used was RESOURCER RPCk 3 ml.

The chromatography was conducted with 0.1% TFA (trifluoroacetic acid) in pump A and 0.1% TFA/90% acetonitrile in pump B at a gradient of from 0% of B to 75% of B within 0 min to 15 min.

As the result, 6 peaks (A-1, . . . , A-6) were confirmed.

Each peak was collected, dried with an evaporator, and redissolved in a small volume of buffer (PBS).

The concentrations of A-1 to A-6 were adjusted to 0.025% with 70% ethanol, respectively, and then 1 ml each was put in cell culture dishes (35 mmϕ, Falcon) made of polystyrene and air-dried.

Control dishes contained only 70% ethanol at 1 ml, followed by air-drying.

Using these dishes, a cell culture experiment was conducted.

The method for cell culture was the same as that in Example 1.

The growth rates of human skin fibroblasts in dishes coated with the peptide fragments from the noncrystalline portion are shown in Table 2.

Among the fragments from the noncrystalline portion, A-6 was excellent for growth, showing ca. 4-fold enhancement compared to the control.

Next, separation of peptides contained in A-6, which showed the best cell growth-promoting activity, according to their molecular weights was performed on Superdex peptide HR10/30 (gel filtration chromatography).

As the result, 7 peaks, A-6-1 to A-6-7, were confirmed. All were under 2,500 in their molecular weights.

Among the 7 peaks, peptides in sharp and distinct 5 peaks (A-6-2, A-6-3, A-6-4, A-6-6, A-6-7) were recovered, and each peptide was coated on cell culture dishes, whereinto the medium and cells were inoculated and cultured for 2 days, followed by the measurement of the cell growth.

The experiment for the cell growth was the same as that in Example 1.

The measurement results of cell growth rates are shown in Table 3.

The growth rates of A-6-2 and A-6-6 after 2-day culture were 1.5 fold higher than the growth of the control, showing excellent cell growth promotion.

The growth rates after 3-day culture exceeded 2 fold.

Subsequently, the amino acid sequences of A-6-2 and A-6-6 were analyzed on LF3000 Protein Sequencer of BI Technologies Japan Ltd., and their amino acid sequences were found to be as follows:

```
A-6-2     Val Ile Thr Thr Asp Ser Asp Gly Asn Glu   (SEQ ID NO. 1)
                          5                   10

A-6-6     Asn Ile Asn Asp Phe Asp Glu Asp           (SEQ ID NO. 2)
                          5
```

Both A-6-2 and A-6-6 were peptides from the N-terminal side of fibroin.

The N-terminal portion is a noncrystalline portion based on the amino acid composition.

Next, the peptides of A-6-2 and A-6-6 were synthesized (contracted out to Hokkaido System Science Co., Ltd.), and physiological activities of the synthesized peptides were determined after a 3-day culture as described above, confirming that these showed cell growth promotion as the extracts from silk protein did.

In addition, when the synthesized A-6-2 and A-6-6 peptides were mixed, its cell growth promotion was superior to that of each peptide present individually in the cell culture.

EXAMPLE 3

Cell Growth Rates of Synthetic Peptides

Synthetic peptides (contracted out to Hokkaido System Science Co., Ltd.), which were derived from a total of 12 sites based on the amino acid sequences of the fibroin H-chain of the domesticated silkworm and the fibroin of *Antheraea yamamai*, were measured for their cell activity.

(1) Peptide Synthesis

Partial peptides from 2 sites of the crystalline portions (SfHC-1, SfHC-2), and partial peptides from 2 sites of the noncrystalline portions (SfHE, SfHA) were picked up from the fibroin of the domesticated silkworm and synthesized.

Further, Ala-repeating site (AfH0) of the crystalline portion and 7 partial peptides (AfH1 to AfH7) of the noncrystalline portions were picked up from the fibroin of *Antheraea yamamai* and synthesized.

The partial peptides from the fibroin H-chain of the domesticated silkworm were 4 kinds, and the partial peptides from the fibroin of *Antheraea yamamai* were 8 kinds (AfH0 to AfH7). Each amino acid sequence of these peptides is shown below.

Partial Peptides from Fibroin H-Chain of Domesticated Silkworm (4 Kinds)

```
SfHC-1    Gly Ala Gly Ala Gly Ser Gly Ala Gly Ala   (SEQ ID NO. 57)
                          5                   10

          Gly Ser Gly Ala Gly Ala Gly Tyr Gly Ala
                          15                  20

          Gly Tyr

SfHC-2    Gly Ala Gly Ala Gly Ser Gly Ala Ala Ser   (SEQ ID NO. 58)
                          5                   10

          Gly Ala Gly Ala Gly Ala Gly Ala Gly Ala
                          15                  20

          Gly Thr

SfHE      Ala Ala Ser Ser Val Ser Ser Ala Ser Ser   (SEQ ID NO. 59)
                          5                   10

          Arg Ser Tyr Asp Tyr Ser Arg Arg Asn Val
                          15                  20

          Arg Lys Asn
```

```
                          -continued
SfHA       Gly Ser Ser Gly Phe Gly Pro Tyr Val Ala    (SEQ ID NO. 60)
                           5               10

           His Gly Gly Tyr Ser Gly Tyr Glu Tyr Ala
                          15               20

           Trp Ser Ser Glu Ser Asp Phe Gly Thr
                          25
```

Partial Peptides from Fibroin of *Antheraea yamamai* (Eight Kinds)

```
AfH 0      Ala Ala Ala Ala Ala Ala Ala Ala Ala Ala    (SEQ ID NO. 61)
                           5               10

AfH 1      Tyr Gly Trp Gly Asp Gly Gly Tyr Gly Ser    (SEQ ID NO. 62)
                           5               10

           Asp Ser

AfH 2      Ser Gly Ala Gly Gly Ser Gly Gly Tyr Gly    (SEQ ID NO. 63)
                           5               10

           Gly Tyr Gly Ser Asp Ser
                          15

AfH 3      Gly Ser Gly Ala Gly Gly Arg Gly Asp Gly    (SEQ ID NO. 64)
                           5               10

           Gly Tyr Gly Ser Gly Ser Ser
                          15

AfH 4      Arg Arg Ala Gly His Asp Arg Ala Ala Gly    (SEQ ID NO. 65)
                           5               10

           Ser

AfH 5      Asp Glu Tyr Val Asp Asn                    (SEQ ID NO. 66)
                           5

AfH 6      Val Glu Thr Ile Val Leu Glu Glu Asp Pro    (SEQ ID NO. 67)
                           5               10

           Tyr Gly His Glu Asp Ile Tyr Glu Glu Asp
                          15               20

AfH 7      Asp Asp Gly Phe Val Leu Asp Gly Gly Tyr    (SEQ ID NO. 68)
                           5               10

           Asp Ser Glu
```

(2) Coating of Synthetic Peptides on Dishes

About 1 mg each of the synthetic peptides was dissolved in 200 μl of PBS. The dissolved peptide solutions were diluted with 70% ethanol to adjust to 0.025% and 0.0025% concentrations, and 1 ml each of these solutions were put in dishes and dried.

SfHC-1, SfHC-2 and SfHE were difficult to dissolve, and therefore, 1 ml of 9 M LiSCN was added to dissolve them.

The dissolved solutions were put into semipermeable membrane tubes and dialyzed against 100 volumes of water with changes of external water every 30 minutes, and then their protein amounts were confirmed by an absorbance at 275 nm.

SfHC-2 is free of tyrosine and the like, and therefore its absorbance measurement was not possible. Since SfHC-1 and SfHE were present approximately in the same amount as they were present before dissolution, SfHC-2 was presumed to be present in the same amount as well and diluted with 70% ethanol in the same way as that used for other peptides, put in dishes and dried.

Further, AfH0 was also hard to dissolve and seemed to be lost upon dialysis due to its small molecular weight, and therefore it was dissolved by stirring well after dilution with 70% ethanol, put in a dish and dried.

(3) Cell Culture

The cells used were human skin fibroblasts (originating from adult normal skin) purchased (frozen) from Sanko Junyaku Co. Ltd.

The culture medium used was the low serum culture medium for human skin fibroblast growth purchased from Kurabo Industries Ltd.

The medium was added at 2 ml per dish, and ca. 80,000 cells were inoculated and cultured for 3 days.

Then, 0.1 ml of Alamer Blue (Iwaki Glass Co.) was added and cultured for 2 hours at 37 degrees C., and the reduced amount of Alamer Blue calculated from the absorbances at 570 nm and 600 nm was correlated with viable cell number.

The method of these measurements for cell culture is the same as that in Example 1.

The results are shown in Tables 4 and 5.

As to the fibroin from the domesticated silkworm, the partial peptides of the noncrystalline portions, SfHE and SfHA, were higher in the growth rate compared to those of the partial peptides of the crystalline portions, SfHC-1 and SfHC-2, and showed more than 2-fold higher values than the control value, indicating that the partial peptides of the noncrystalline portions or their mixtures are SDFGP.

There was little activity in AfH0 which is a partial peptide of the crystalline portion of the fibroin from *Antheraea yamamai*, and the higher concentration (0.025%) was lower in the growth rate, suggesting an inhibition of the cell growth.

The synthetic partial peptides of the noncrystalline portion, AfH1 to AfH7, showed cell growth promotion with differences in their growth rates.

For example, both of AfH3 and AfH6 contain one basic amino acid residue, respectively. Since AfH3 contains less acidic amino acid residues and AfH6 contains more acidic amino acid residues, AfH6 showed higher cell growth promotion.

Particularly, AfH1, AfH5, AfH6 and AfH7 showed excellent cell growth promotion, and all of these are SDFGP obtained by synthesis.

As shown in Table 5, not all partial peptides derived from the noncrystalline portions become SDFGP with high growth rates.

As shown in Table 6, this is due to the differences in the chemical structures of side chains of the amino acids constituting each peptide.

EXAMPLE 4

Cell Growth Activity of Synthetic Peptides

Based on the results in Examples 1 to 3, synthetic peptides (contracted out to Hokkaido System Science Co., Ltd.) having acidic amino acids and polar non-charged amino acids, which were supposed to show a cell growth activity, as the main components were measured for their fibroblast growth-promoting activity.

The measurements for the cell growth activity were carried out by a method similar to that in Example 1.

The cell culture was performed for 3 days, and the results obtained at a peptide concentration of 0.025 μg/$cm^2$ are shown in Table 7.

As to glutamic acid, four or more sequential residues were excellent for cell growth activity.

EXAMPLE 5

Promotion of Cell Adhesion and Proliferation by Synthetic Peptides

The cell growth activities of synthetic peptides originating from silk protein, synthetic peptides having mainly acidic amino acids or polar non-charged amino acids, or the like were further measured in detail by dividing into cell adhesion and cell proliferation.

This method partly differs from the method in (3) Cell culture of Example 1.

In the present cell culture, the cells used were human skin fibroblasts (originating from adult normal skin) purchased (frozen) from Sanko Junyaku Co. Ltd.

The culture medium used was the low serum culture medium for human skin fibroblast growth purchased from Kurabo Industries Ltd. (Medium 106S 500 ml).

The medium 106S is a basal medium for skin fibroblasts.

LSGS (low serum growth supplement) was not used here.

In the measurement of adhesion, the cells floating in the medium at 5 hours after inoculation of cells into the medium were removed, and the viable cell number adhering to the bottom of a dish was measured.

In the measurement of proliferation, the viable cell number at 3 days after inoculation of cells into the medium was measured.

Besides the cell culture method, coating of peptides on cell culture dishes, measurement of viable cell number with Alamer Blue dye, and the like were carried out as described in Example 1.

The results obtained for adhesion and those obtained for proliferation are shown in Tables 8 and 9, respectively, in comparison with the viable cell number of the control (100%) where no peptide was coated on dishes.

Namely, Table 8 shows adhesion after culturing human skin fibroblasts for 5 hours in dishes coated with various peptides.

Here, the synthetic peptides are shown either by symbol or amino acid sequence.

In this case, the concentration of each peptide coated on dishes was 0.025 μg/$cm^2$.

The adhesion rate (%) in the case where no peptide was coated was set at 100.

Table 9 shows the proliferation after 3-day culturing of human skin fibroblasts in dishes coated with various peptides.

Here, the synthetic peptides are shown either by symbol or amino acid sequence.

In this case, the concentration of each peptide coated on dishes was 0.025 μg/$cm^2$.

The growth rate (%) in the case where no peptide was coated was set at 100.

It should be noted that the viable cell number in the control in 3-day culturing increased about 150% during the culture and the control value (100%) was based on the viable cell number after 3-day culture.

Accordingly, when there was no increase or decrease in the cell number after 3-day culturing, the growth rate would become about 70%.

TABLE 1

Growth rates of human skin fibroblasts in dishes coated with crystalline portion and noncrystalline portion

| | Concentration | Growth rate (%) | Significant difference from control; Confidence rate (%) |
|---|---|---|---|
| Control | | 100 ± 8.6* | |
| Crystalline | 0.025% | 149 ± 5.6 | 99.9 |
| portion (C') | 0.0025% | 174 ± 8.8 | 99.0 |
| Noncrystalline | 0.025% | 259 ± 10.3 | 99.0 |
| portion (A') | 0.0025% | 164 ± 5.0 | 99.0 |

(*Standard deviation)

TABLE 2

Growth of human skin fibroblasts in dishes coated with peptide fragments from noncrystalline portion

| | Growth rate (%) | Significant difference from control; Confidence rate (%) |
|---|---|---|
| Control | 100 ± 15.0* | |
| A-1 | 124 ± 6.0 | <95 |
| A-2 | 171 ± 3.5 | 99 |
| A-3 | 148 ± 4.5 | 95 |
| A-4 | 215 ± 12.0 | 99 |

TABLE 2-continued

Growth of human skin fibroblasts in dishes coated with peptide fragments from noncrystalline portion

| | Growth rate (%) | Significant difference from control; Confidence rate (%) |
|---|---|---|
| A-5 | 269 ± 13.0 | 99.9 |
| A-6 | 389 ± 12.2 | 99.9 |

(*Standard deviation)

TABLE 3

Growth rates of human skin fibroblasts in dishes coated with 5 fragments obtained from the peptide chain (Table 2, A-6)

| | Growth rate (%) | Significant difference from control; Confidence rate (%) |
|---|---|---|
| Control | 100 ± 6.1* | |
| A-6-2 | 153 ± 2.7 | 99.9 |
| A-6-3 | 139 ± 15.2 | 98.0 |
| A-6-4 | 105 ± 12.2 | <95.0 |
| A-6-6 | 159 ± 6.6 | 99.0 |
| A-6-7 | 124 ± 4.3 | 99.0 |

(*Standard deviation)

TABLE 4

Growth of human skin fibroblasts in dishes coated with synthetic partial peptides of fibroin of domesticated silkworm

| | Concentration | Growth rate (%) | Significant difference from control; Confidence rate (%) |
|---|---|---|---|
| Control | | 100 ± 1.5* | |
| SfHC-1 | 0.025% | 194 ± 2.3 | 99.9 |
| | 0.0025% | 146 ± 6.0 | 99.9 |
| SfHC-2 | 0.025% | 136 ± 1.0 | 99.9 |
| | 0.0025% | 116 ± 8.9 | 95 |
| SfHE | 0.025% | 243 ± 3.9 | 99.9 |
| | 0.0025% | 198 ± 12.5 | 99 |
| SfHA | 0.025% | 316 ± 5.7 | 99.9 |
| | 0.0025% | 321 ± 6.2 | 99.9 |

(*Standard deviation)

TABLE 5

Growth of human skin fibroblasts in dishes coated with synthetic partial peptides of fibroin of *Antheraea yamamai*

| | Concentration | Growth rate (%) | Significant difference from control; Confidence rate (%) |
|---|---|---|---|
| Control | | 100 ± 26.5* | |
| AfH0 | 0.025% | 100 ± 7.4 | <50 |
| | 0.0025% | 152 ± 6.1 | 95 |
| AfH1 | 0.025% | 396 ± 4.0 | 99 |
| | 0.0025% | 179 ± 13.5 | 98 |
| AfH2 | 0.025% | 196 ± 9.4 | 99 |
| | 0.0025% | 118 ± 14.7 | 60 |
| AfH3 | 0.025% | 194 ± 24.5 | 98 |
| | 0.0025% | 111 ± 9.0 | <50 |
| AfH4 | 0.025% | 133 ± 8.7 | 80 |
| | 0.0025% | 113 ± 4.8 | 50 |
| AfH5 | 0.025% | 344 ± 7.7 | 99.9 |
| | 0.0025% | 192 ± 11.3 | 99 |
| AfH6 | 0.025% | 264 ± 9.0 | 99.9 |
| | 0.0025% | 152 ± 9.0 | 95 |

TABLE 5-continued

Growth of human skin fibroblasts in dishes coated with synthetic partial peptides of fibroin of *Antheraea yamamai*

| | Concentration | Growth rate (%) | Significant difference from control; Confidence rate (%) |
|---|---|---|---|
| AfH7 | 0.025% | 284 ± 25.1 | 99.9 |
| | 0.0025% | 155 ± 5.3 | 95 |

(*Standard deviation)

TABLE 6

Percentage of each amino acid group constituting synthetic peptides and cell growth rates (The cell growth rates in Tables 4 and 5 are values obtained at higher peptide concentration (0.025%))

| Partial peptide of fibroin of domesticated silkworm and *Antheraea yamamai* | Cell growth rate (%) | Number of residues in peptide | Gly + Ala Number | Gly + Ala (%) | Basic amino acids Number | Basic amino acids (%) |
|---|---|---|---|---|---|---|
| SfHC-1 | 194 | 22 | 18 | 82 | 0 | 0 |
| SfHC-2 | 136 | 22 | 19 | 86 | 0 | 0 |
| SfHE | 243 | 23 | 3 | 13 | 5 | 4 |
| SfHA | 316 | 29 | 9 | 31 | 1 | 13 |
| AfH0 | 100 | 10 | 10 | 100 | 0 | 0 |
| AfH1 | 396 | 12 | 5 | 50 | 0 | 0 |
| AfH2 | 196 | 16 | 9 | 56 | 0 | 0 |
| AfH3 | 194 | 17 | 10 | 59 | 1 | 6 |
| AfH4 | 133 | 11 | 5 | 46 | 4 | 36 |
| AfH5 | 344 | 6 | 0 | 17 | 0 | 0 |
| AfH6 | 264 | 20 | 1 | 35 | 1 | 5 |
| AfH7 | 284 | 13 | 3 | 46 | 0 | 0 |

TABLE 7

Cell growth activity of synthetic peptides

| Amino acid or amino acid sequence of peptides | | Cell growth rate (%) |
|---|---|---|
| Glu | | 69 |
| Glu Glu | | 159 |
| Glu Glu Glu Glu | (SEQ ID NO. 78) | 231 |
| Glu Glu Glu Glu Glu Glu | (SEQ ID NO. 79) | 346 |
| Glu Glu Glu Glu Glu Glu Glu Glu Glu Glu | (SEQ ID NO. 84) | 254 |
| Tyr Tyr | | 113 |
| Tyr Tyr Tyr Tyr | (SEQ ID NO. 85) | 156 |
| Tyr Tyr Tyr Tyr Tyr Tyr | (SEQ ID NO. 82) | 239 |
| Asp Glu Asp Glu Asp Glu | (SEQ ID NO. 71) | 322 |
| Glu Tyr Glu Tyr Glu Tyr | (SEQ ID NO. 80) | 207 |
| Glu Glu Tyr Glu Glu Tyr | (SEQ ID NO. 81) | 212 |

TABLE 8

Adhesion after 5 hour-culture of human skin fibroblasts in dishes coated with each peptide

| Synthetic peptide | Adhesion rate (%) |
|---|---|
| SfHC-1 | 130 |
| SfHC-2 | 138 |

TABLE 8-continued

| Adhesion after 5 hour-culture of human skin fibroblasts in dishes coated with each peptide | |
|---|---|
| Synthetic peptide | Adhesion rate (%) |
| SfHA | 205 |
| SfHE | 190 |
| AfH0 | 131 |
| AfH1 | 169 |
| AfH2 | 149 |
| AfH3 | 174 |
| AfH4 | 151 |
| AfH5 | 234 |
| AfH6 | 135 |
| AfH7 | 153 |
| Asp Glu Asp Glu Asp Glu (SEQ ID NO. 71) | 229 |

TABLE 9

| Growth after 3 day-culture of human skin fibroblasts in dishes coated with each peptide | |
|---|---|
| Synthetic peptide | Growth rate (%) |
| SfHC-1 | 71 |
| SfHC-2 | 97 |
| SfHA | 159 |
| SfHE | 126 |
| AfH0 | 102 |
| AfH1 | 94 |
| AfH2 | 71 |
| AfH3 | 69 |
| AfH4 | 96 |
| AfH5 | 108 |
| AfH6 | 77 |
| AfH7 | 89 |

What is claimed is:

1. A peptide consisting of up to forty amino acid residues and comprising an amino acid sequence selected from the group consisting of SEQ ID NOS. 3–8.

2. A cell growth-promoting agent comprising the peptide of claim 1.

3. A cell adhesion agent comprising the peptide of claim 1.

4. A wound healing promoting agent comprising the peptide of claim 1.

5. A cosmetic material comprising the peptide of claim 1.

6. A cell culture substrate comprising the peptide of claim 1.

* * * * *